US010030269B2

(12) United States Patent
Anastassiou

(10) Patent No.: US 10,030,269 B2
(45) Date of Patent: Jul. 24, 2018

(54) BIOMARKERS, METHODS, AND COMPOSITIONS FOR INHIBITING A MULTI-CANCER MESENCHYMAL TRANSITION MECHANISM

(71) Applicant: THE TRUSTEES OF COLUMBIA UNIVERSITY IN THE CITY OF NEW YORK, New York, NY (US)

(72) Inventor: Dimitris Anastassiou, Tenafly, NJ (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 228 days.

(21) Appl. No.: 14/150,740

(22) Filed: Jan. 8, 2014

(65) Prior Publication Data

US 2014/0228236 A1    Aug. 14, 2014

Related U.S. Application Data

(63) Continuation of application No. PCT/US2012/045958, filed on Jul. 9, 2012.

(60) Provisional application No. 61/506,075, filed on Jul. 9, 2011.

(51) Int. Cl.
*C12Q 1/68* (2018.01)
*C12Q 1/6881* (2018.01)
*C12Q 1/6886* (2018.01)

(52) U.S. Cl.
CPC ......... *C12Q 1/6881* (2013.01); *C12Q 1/6886* (2013.01); *C12Q 2600/112* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 5,006,309 | A | 4/1991 | Khalil et al. |
| 5,089,424 | A | 2/1992 | Khalil et al. |
| 5,143,854 | A | 9/1992 | Pirrung et al. |
| 5,384,261 | A | 1/1995 | Winkler et al. |
| 5,424,186 | A | 6/1995 | Fodor et al. |
| 5,445,934 | A | 8/1995 | Fodor et al. |
| 5,547,839 | A | 8/1996 | Dower et al. |
| 5,677,195 | A | 10/1997 | Winkler et al. |
| 5,708,153 | A | 1/1998 | Dower et al. |
| 5,744,305 | A | 4/1998 | Fodor et al. |
| 5,770,358 | A | 6/1998 | Dower et al. |
| 5,789,162 | A | 8/1998 | Dower et al. |
| 5,800,992 | A | 9/1998 | Fodor et al. |
| 5,856,174 | A | 1/1999 | Lipshutz et al. |
| 5,888,819 | A | 3/1999 | Goelet et al. |
| 5,922,591 | A | 7/1999 | Anderson et al. |
| 5,981,176 | A | 11/1999 | Wallace |
| 6,040,193 | A | 3/2000 | Winkler et al. |
| 6,395,472 | B1 | 5/2002 | Leary et al. |
| 6,770,751 | B2 | 8/2004 | Southern et al. |
| 2007/0275404 | A1 | 11/2007 | Matthijs et al. |
| 2008/0233585 | A1 | 9/2008 | Burgess et al. |
| 2009/0023149 | A1 | 1/2009 | Knudsen |
| 2009/0233286 | A1 | 9/2009 | Segara et al. |
| 2009/0274667 | A1* | 11/2009 | Temple ............... C12N 5/0607 424/93.7 |
| 2009/0286850 | A1 | 11/2009 | Shaaban et al. |
| 2010/0088775 | A1 | 4/2010 | New-Goodall et al. |
| 2010/0221218 | A1* | 9/2010 | Kan ..................... C12N 5/0693 424/85.6 |
| 2011/0190378 | A1 | 8/2011 | Wang et al. |
| 2013/0040852 | A1 | 2/2013 | Anastassiou et al. |
| 2014/0031251 | A1* | 1/2014 | Yeatman ............. C12Q 1/6886 506/9 |

FOREIGN PATENT DOCUMENTS

WO    WO-2009097136 A1 *  6/2009

OTHER PUBLICATIONS

Handbook of Chemistry and Physics, 49th Edition, 1968, Weast (ed.), The Chemical Rubber Co., Cleveland, Ohio, p. A-245.*
International Search Report and Written Opinion for PCT/US2012/045958, dated Jan. 23, 2013.
International Search Report for PCT/US2011/023256, dated Jun. 16, 2011.
Anastassiou, et al., "Human Cancer Cells Express Slug-Based Epithelial-Mesenchymal Transition Gene Expression Signature Ontained in vivo", *BMC Cancer*, 11:529 (2011).
Aoyagi, et al., "Artificially Induced Epithelial-Mesenchymal Transition in Surgical Subjects: Its Implications in Clinical and Basic Cancer Research", *PlosOne*, 6(4):e18196 (2011).
Bignotti, et al., "Gene Expression Profile of Ovarian Serous Papillary Carcinomas: Identification of Metastasis-Associated Genes", *American Journal of Obstetrics & Gynecology*, 196:245.e1-245.e11 (2007).

(Continued)

*Primary Examiner* — James Martinell
(74) *Attorney, Agent, or Firm* — Baker Botts L.L.P.

(57) ABSTRACT

The present invention relates to the discovery that the modulation of particular microRNAs can be employed to inhibit a mesenchymal transition that, in certain instances, correlates with resistance to therapy and recurrence as the corresponding cells acquire properties of stem cells as they start undergoing this transition, as well as with invasiveness, e.g., invasion of certain cells of primary tumors into adjacent connective tissue during the initial phase of metastasis. Accordingly, the identification inhibitors of this mechanism, such as inhibitors of certain microRNAs, disclosed herein, can be used for inhibiting the mesenchymal transition to reduce the invasive nature of certain cells of primary cancerous tumors and, in certain instances, to prevent the recurrence of cancer by inhibiting the induction of stem cell-like features in certain cancer cells.

6 Claims, 3 Drawing Sheets

(56) References Cited

OTHER PUBLICATIONS

Figure 1:
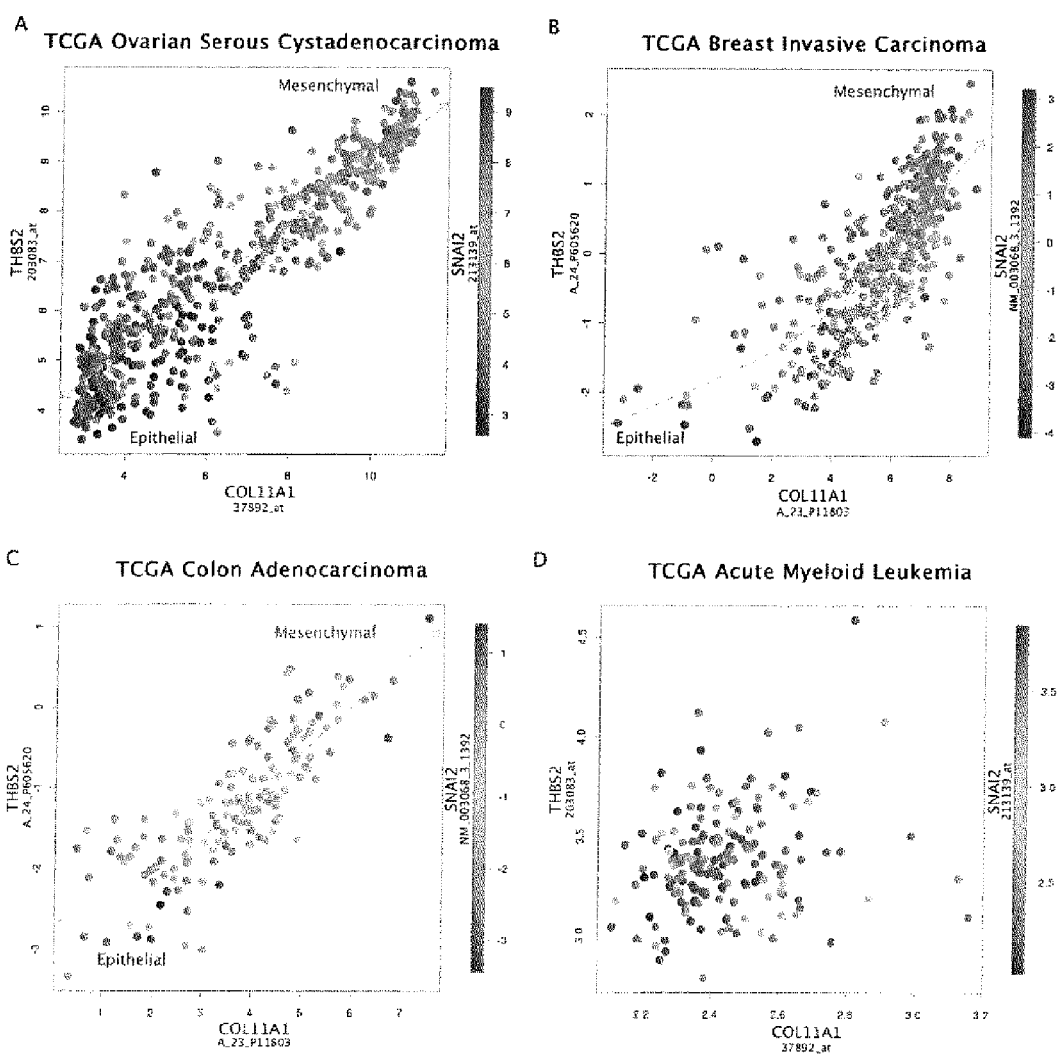

Blick, et al., "Epithelial Mesenchymal Transition Traits in Human Breast Cancer Cell Lines Parallel the $CD44^{hi}/CD24^{lo/-}$ Stem Cell Phenotype in Human Breast Cancer", *J Mammary Gland Biol. Neoplasia*, 15:235-252 (2010).
Castilla, et al., "Micro-RNA Signature of the Epithelial-Mesenchymal Transition in Endometrial Carcinosarcoma", *Journal of Pathology*, 223:72-80 (2011).
Cheng, et al., "A Multi-Cancer Mesenchymal Transition Gene Expression Signature is Associated with Prolonged Time to Recurrence in Glioblastoma", *PlosOne*, 7(4):e34705 (2012).
Chong, et al., "Great Potential of a Panel of Multiple hMTH1, SPD, ITGA11 and COL11A1 Markers for Diagnosis of Patients with Non-Small Cell Lung Cancer", *Oncology Reports*, 16(5):981-988 (2006).
Creighton, et al., "Residual Breast Cancers after Conventional Therapy Display Mesenchymal as Well as Tumor-Initiating Features", *PNAS*, 106(33):13820-13825 (2009).
Jorissen, et al., "Metastasis-Associated Gene Expression Changes Predict Poor Outcomes in Patients with Dukes' Stage B and C Colorectal Cancer", *Clinical Cancer Research*, 15(24):7642-7651 (2009).
Jukic, et al., "Microrna Profiling Analysis of Differences Between the Melanoma of Young Adults and Older Adults", *Journal of Translational Medicine*, 8:27 (2010).
Kessenbrock, et al., "Matrix Metalloproteinases: Regulators of the Tumor Microenviroment", *Cell*, 141(1):52-67 (2010).
Lien, et al., "Molecular Signatures of Metaplastic Carcinoma of the Breast by Large-Scale Transcriptional Profiling: Identification of Genes Potentially Related to Epithelial-Mesenchymal Transition", *Oncogene*, 26:7859-7871 (2007).
Ma, et al., "Gene Expression Profiling of the Tumor Microenviroment During Breast Cancer Progression", *Breast Cancer Research*, 11:R7 (2009).
Mueller, et al., "miRNA Expression Profiling in Melanocytes and Melanoma Cell Lines Reveals miRNAs Associated with Formation and Progression of Malignant Melanoma", *Journal of Investigative Dermatology*, 129:1740-1751 (2009).
Newkirk, et al., "Snai2 Expression Enhances Ultraviolet Radiation-Induced skin Carcinogenesis", *The American Journal of Pathology*, 171(5):1629-1639 (2007).
Ogino, et al., "Follistatin Suppresses the Production of Experimental Multiple-Organ Metastasis by Small Cell Lung Cancer Cells in Natural Killer Cell-Depleted SCID Mice", *Clinical Cancer Research*, 14:660-667 (2008).
Parker, et al., "Alterations in Vascular Gene Expression in Invasive Breast Carcinoma", *Cancer Research*, 64:7857-7866 (2004).
Schmalbach, et al., "Molecular Profiling and the Identification of Genes Associated with Metastatic Oral Cavity/Pharynx Squamous Cell Carcinoma", *Archives of Otolaryngology*, 130(3):295-302 (2004).
Smith, et al., "Experimentally Derived Metastasis Gene Expression Profile Predicts Recurrence and Death in Patients with Colon Cancer", *Gastroenterology*, 138(3):958-968 (2010).
Talmadge, "Follistatin as an Inhibitor of Experimental Metastasis", *Clinical Cancer Research*, 14:624-626 (2008).
Tothill, et al., "Novel Molecular Subtypes of Serous and Endometrioid Ovarian Cancer Linked to Clinical Outcome", *Clinical Cancer Research*, 14:5198-5208 (2008).
Vecchi, et al., "Gene Expression Analysis of Early and Advanced Gastric Cancers", *Oncogene*, 26(29):4284-4294 (2007).
Watkinson, et al., "Inference of Regulatory Gene Interactions from Expression Data Using Three-Way Mutual Information", *The Challenges of Systems Biology: Ann. NY Acad. Sci.*, 1158:302-313 (2009).
Weinberg RA., "The Biology of Cancer", *Garland Science*, pp. 600-602 (2007).
Worley, et al., "Micro-RNAs Associated With Metastasis in Uveal Melanoma Identified by Multiplexed Microarray Profiling", *Melanoma Research*, 18:184-190 (2008).
International Search Report and Written Opinion for PCT/US2013/025709, dated May 13, 2013.
Denby, et al., "miR-21 and miR-214 are consistently modulated during renal injury in rodent models", *The American Journal of Pathology*, 179(2):661-672 (2011).
Hong, et al., "A 'metastasis-prone' signature for early-stage mismatch-repair proficient sporadic colorectal cancer patients and its implications for possible therapeutics", *Clin Exp. Metastasis*, 27(2):83-90 (2010).
Wong, et al., "Combination of microarray profiling and protein-protein interaction databases delineates the minimal discriminators as a metastasis network for esophageal squamous cell carcinoma", *International Journal of Oncology*, 34:117-128 (2009).

\* cited by examiner

BIOMARKERS, METHODS, AND COMPOSITIONS FOR INHIBITING A MULTI-CANCER MESENCHYMAL TRANSITION MECHANISM

CROSS REFERENCE TO RELATED APPLICATIONS

The present application is a continuation of PCT Application No. PCT/US12/045,958, filed Jul. 9, 2012, which claims priority to U.S. Provisional Application No. 61/506,075, filed on Jul. 9, 2011, the disclosures of each of which are incorporated by reference herein in their entirety.

SEQUENCE LISTING

The specification further incorporates by reference the Sequence Listing submitted herewith via EFS on Apr. 28, 2014. Pursuant to 37 C.F.R. § 1.52(e)(5), the Sequence Listing text file, identified as 0700505140SeqList.txt, is 32,768 bytes and was created on Apr. 28, 2014.

1. Introduction

The present invention relates to the discovery that specific differentially-expressed genes in cancer cells are associated with epithelial-mesenchymal transition (EMT) and that, in certain instances, such EMT correlates with invasiveness, e.g., invasion of certain cells of primary tumors into adjacent connective tissue during the initial phase of metastasis. Accordingly, the identification of biomarkers associated with this mechanism, such as the specific differentially-expressed genes disclosed herein, can be used for identifying the initiation of EMT and, in certain instances, diagnosing and staging particular cancers, for monitoring cancer progress/regression, for developing therapeutics, e.g., the microRNA inhibitors disclosed herein, and for predicting the appropriateness of certain treatment strategies.

2. Background of the Invention

As used herein, the term epithelial-mesenchymal transition (EMT) relates to a biologic process that allows a cancer cell to undergo multiple biochemical changes enabling it to assume a mesenchymal cell phenotype, e.g., enhanced migratory capacity, invasiveness, elevated resistance to apoptosis, and greatly increased production of ECM components. (Kalluri R, J. Clin. Invest. 2009; 119(6):1420). As used herein the term EMT refers to mesenchymal transitions generally and therefore is not limited to cells of epithelial origin, but includes non-epithelial cells, e.g., neuroblastoma cells. As used herein, a gene expression signature correlating with the observed EMT is referred to as "the EMT signature." There is currently great interest in characterizing and making use of the biological mechanism underlying EMT, as well as cancer invasion and subsequent metastasis, and this interest is addressed by the present invention.

3. Summary of the Invention

The present invention relates to biomarkers which constitute an EMT signature and their use in identifying EMT, particularly early EMT, as well as diagnosing and staging a variety of cancers. It is based, at least in part, on the discovery that identifying the differential expression of certain genes indicates the initiation of EMT and, in certain instances, indicates a diagnosis and/or stage of a variety of cancers with a high degree of specificity. Accordingly, in various embodiments, the present invention provides for methods of diagnosis, diagnostic kits, as well as methods of treatment that include an assessment of biomarker status in a subject.

In certain embodiments, the present invention relates to the discovery that because the differential expression of certain genes can function as a marker for EMT, such expression profiles can be used to screen for therapeutics capable of inhibiting such transition. Accordingly, in various embodiments, the present invention provides for methods of screening therapeutics for their anti-EMT potential as well as screening kits.

In certain embodiments, the present invention is directed to methods of identifying EMT in a subject comprising determining, in a sample from the subject, the expression level, relative to a normal subject, of a Snail Homolog 2 ("SNAI2"; GenBank U97060) gene product wherein overexpression of a SNAI2 gene product indicates that the subject has initiated EMT.

In certain embodiments, the present invention is directed to methods of identifying EMT in a subject comprising determining, in a sample from the subject, the expression level, relative to a normal subject, of at least one gene product selected from the group consisting of at least one of, at least two of, at least three of, at least four of, or at least five, at least six, or at least all seven of the following: SNAI2; Lumican ("LUM"; GenBank BT006707); Decorin ("DCN"; GenBank AF138300); Collagen, Type I, Alpha 1 ("COL1A1"; GenBank Z74615); Collagen, Type I, Alpha 2 ("COL1A2"; GenBank Z74616); Collagen, Type III, Alpha 1 ("COL3A1"; GenBank X15332); and Collagen, Type VI, Alpha 3 ("COL6A3"; GenBank X52022), wherein overexpression of said gene product or products indicates that the subject has initiated EMT.

In certain embodiments, the biomarker signature of EMT includes overexpression of at least one of, at least two of, at least three of, at least four of, or at least five, at least six, or at least all seven of the following proteins: SNAI2, LUM, DCN, COL1A1, COL1A2, COL3A1, and COL6A3, in combination with differential expression of one or more microRNAs selected from the group consisting of: microRNA 214 ("miR-214"; NCBI NR_029627); microRNA 199a ("miR-199a"; NCBI NR_029586); and microRNA 199b ("miR-199b"; NCBI NR_029619).

In certain of such embodiments, the expression level is determined by a method comprising a step wherein the sample is processed so that cells in the sample are lysed. In certain of such embodiments, the method comprises the further step of purifying, which can encompass at least partial to substantial purification cellular gene products and exposing said gene products to a detection agent. In certain embodiments, the method comprises the further step of purifying, again partially to substantially, cellular nucleic acid and exposing said nucleic acid to a detection agent. In certain embodiments, the method further comprises a step of detecting fatty acid binding protein 4 ("FABP4"; GenBank 302874) expression, wherein altered FABP4 expression, i.e., either an increase or decrease in FABP4 expression, is indicative of EMT.

In certain embodiments, the present invention is directed to methods for identifying an agent that inhibits EMT in a subject, comprising exposing a test agent to cells expressing an EMT signature, wherein if the test agent decreases overexpression of one or more than one genes in the signature, the test agent may be used as a therapeutic agent in inhibiting such a transition. In certain embodiments, the EMT signature comprises overexpression of at least one gene product expressed by a gene selected from the group consisting of: SNAI2, LUM, DCN, COL1A1, COL1A2, COL3A1, and COL6A3. In certain embodiments, the method further comprises a step of detecting FABP4 expression, wherein altered FABP4 expression, i.e., either an increase or decrease in FABP4 expression, is indicative of EMT.

In certain embodiments, the present invention is directed to kits comprising: (a) a labeled reporter molecule capable of specifically interacting with an EMT signature gene product; (b) a control or calibrator reagent, and (c) instructions describing the manner of utilizing the kit.

In certain embodiments, the present invention is directed to kits comprising: (a) a conjugate comprising an antibody that specifically interacts with an EMT signature antigen attached to a signal-generating compound capable of generating a detectable signal; (b) a control or calibrator reagent, and (c) instructions describing the manner of utilizing the kit. In certain of such embodiments, the present invention is directed to kits comprising: a EMT signature antigen-specific antibody, where the EMT signature antigen bound by said antibody comprises or is otherwise derived from a protein encoded by SNAI2, LUM, DCN, COL1A1, COL1A2, COL3A1, or COL6A3. In certain embodiments, the method further comprises a step of detecting FABP4 expression, wherein altered FABP4 expression, i.e., either an increase or decrease in FABP4 expression, is indicative of EMT. In non-limiting specific embodiments, in a panel provided in said kit, antigens listed above represent up to about 20 percent, or up to about 30 percent, or up to about 50 percent, or up to about 75 percent, or up to about 90 percent, or up to about 100 percent, of the antigens in the entire panel to be tested. Said kit may optionally further comprise one or more positive and/or one or more negative control sample(s).

In certain embodiments, the present invention is directed to kits comprising: (a) a nucleic acid capable of hybridizing to an EMT signature nucleic acid; (b) a control or calibrator reagent; and (c) instructions describing the manner of utilizing the kit. In certain of such embodiments, the kits comprise: (a) a nucleic acid sequence comprising: (i) a target-specific sequence that hybridizes specifically to an EMT signature nucleic acid, and (ii) a detectable label; (b) a primer nucleic acid sequence; (c) a nucleic acid indicator of amplification; and. (d) instructions describing the manner of utilizing the kit. In certain of such embodiments, the present invention is directed to kits comprising a nucleic acid that hybridizes specifically to an EMT signature nucleic acid comprising or otherwise derived from of at least one of, at least two of, at least three of, at least four of, or at least five, at least six, or at least all seven of the following: SNAI2, LUM, DCN, COL1A1, COL1A2, COL3A1, and COL6A3. In certain embodiments, the method further comprises a step of detecting FABP4 expression, wherein altered FABP4 expression, i.e., either an increase or decrease in FABP4 expression, is indicative of EMT. In non-limiting specific embodiments, in a panel provided in said kit, EMT signature nucleic acids listed above represent up to about 20 percent, or up to about 30 percent, or up to about 50 percent, or up to about 75 percent, or up to about 90 percent, or up to about 100 percent, of nucleic acids in the entire panel to be tested. Said kit may optionally further comprise one or more positive and/or one or more negative control sample(s).

The invention is further based, in part, on the discovery that because the differential expression of certain genes can function as marker for the acquisition of invasive potential, such expression profiles can be used to screen for therapeutics capable of inhibiting acquisition of metastatic potential. Accordingly, in various embodiments, the present invention provides for methods of screening therapeutics for their anti-invasion and/or anti-metastatic properties as well as screening kits.

In certain embodiments, the present invention is directed to methods of diagnosing invasive cancer in a subject comprising determining, in a sample from the subject, the overexpression of at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, at least twenty five, at least twenty six, at least twenty seven, at least twenty eight, at least twenty nine, or all thirty of the following: Collagen, Type XI, Alpha 1 ("COL11A1"; GenBank J04177); thrombospondin ("THBS2"; NCBI NM_003247); Collagen, Type V, Alpha 2 ("COL5A2"; GenBank Y14690); Collagen, Type V, Alpha 1 ("COL5A1"; GenBank D90279); Versican ("VCAN"; GenBank X15998); COL1A1; COL3A1; Fibronectin ("FN1"; NCBI NM_002026); sulfatase 1 ("SULF1"; GenBank AB029000); Fibrillin 1 ("FBN1"; GenBank X63556); Asporin ("ASPN"; GenBank AF316824); Secreted Protein, Acidic, Cysteine-Rich ("SPARC"; NCBI NM_003118); Cathepsin K ("CTSK"; GenBank BC016058); Matrix Metallopeptidase 2 ("MMP2"; NCBI NM_001127891); Biglycan ("BGN"; GenBank AK092954); LUM; Lysyl Oxidase-Like 2 ("LOXL2"; GenBank U89942); COL6A3; TIMP metallopeptidase inhibitor 3 ("TIMP3"; NCBI NM_000362); cadherin 11, type 2 ("CDH11"; GenBank D21255); Serpin Peptidase Inhibitor, Clade F, Member 1 ("SERPINF1"; GenBank M76979); Endothelin Receptor Type A ("EDNRA"; GenBank D90348); Actin, Alpha 2, Smooth Muscle, Aorta ("ACTA2"; GenBank X13839); Platelet-Derived Growth Factor Receptor, Beta Polypeptide ("PDGFRB"; GenBank M21616); SNAI2; Lectin, Galactoside-Binding, Soluble, 1 ("LGALS1"; NCBI NM_002305); Glycosyltransferase 8 Domain Containing 2 ("GLT8D2"; GenBank BC022343); Nidogen 2 ("NID2"; GenBank AB009799); Paired Related Homeobox 1 ("PRRX1"; GenBank M95929); and Vimentin ("VIM"; GenBank M14144), wherein overexpression of said gene product or products indicates that the subject has invasive cancer.

In certain embodiments, the present invention is directed to methods of diagnosing invasive cancer in a subject comprising determining, in a sample from the subject, the expression level, relative to a normal subject, of at least one gene product selected from the group consisting of at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, at least twenty five, at least twenty six, at least twenty seven, at least twenty eight, at least twenty nine, or all thirty of the following: COL11A1, THBS2, COL5A2, COL5A1, VCAN, COL1A1, COL3A1, FN1, SULF1, FBN1, ASPN, SPARC, CTSK, MMP2, BGN, LUM, LOXL2, COL6A3, TIMP3, CDH11, SERPINF1, EDNRA, ACTA2, PDGFRB, SNAI2, LGALS1, GLT8D2, NID2, PRRX1, and VIM, wherein overexpression of said gene product or products indicates that the subject has invasive cancer. In certain of such embodiments, the expression level is determined by a method comprising processing the sample so that cells in the sample are lysed. In certain of such embodiments, the method comprises the further step of at purifying, partially or substantially, cell gene products and exposing said proteins to a detection agent. In certain embodiments, the method comprises the further step of at purifying, partially or substantially, cell nucleic acid and exposing said nucleic acid to a detection agent. In certain of such embodiments, the method comprises the further step of determining the expression level of SNAI1, where a determination that SNAI1 is not overexpressed and the other gene products are overexpressed indicates that the subject has invasive cancer. In certain embodiments, the method further comprises a step of detecting FABP4 expression, wherein altered FABP4 expression, i.e., either an increase or decrease in FABP4 expression, is indicative of EMT.

In certain embodiments, the present invention is directed to methods for identifying an agent that inhibits cancer invasion in a subject, comprising exposing a test agent to cancer cells expressing an EMT signature, wherein if the test agent decreases overexpression of genes in the signature, the test agent may be used as a therapeutic agent in inhibiting invasion of a cancer. In certain embodiments, the EMT signature employed in method comprises overexpression of at least one gene product selected from the group consisting of at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, at least twenty five, at least twenty six, at least twenty seven, at least twenty eight, at least twenty nine, or all thirty of the following: COL11A1, THBS2, COL5A2, COL5A1, VCAN, COL1A1, COL3A1, FN1, SULF1, FBN1, ASPN, SPARC, CTSK, MMP2, BGN, LUM, LOXL2, COL6A3, TIMP3, CDH11, SERPINF1, EDNRA, ACTA2, PDGFRB, SNAI2, LGALS1, GLT8D2, NID2, PRRX1, and VIM. In certain embodiments, the method further comprises a step of detecting FABP4 expression, wherein altered FABP4 expression, i.e., either an increase or decrease in FABP4 expression, is indicative of EMT.

In certain embodiments, the present invention is directed to kits comprising: (a) a labeled reporter molecule capable of specifically interacting with an EMT signature gene product; (b) a control or calibrator reagent, and (c) instructions describing the manner of utilizing the kit.

In certain embodiments, the present invention is directed to kits comprising: (a) a conjugate comprising an antibody that specifically interacts with an EMT signature antigen attached to a signal-generating compound capable of generating a detectable signal; (b) a control or calibrator reagent, and (c) instructions describing the manner of utilizing the kit. In certain of such embodiments, the present invention is directed to kits comprising: a EMT signature antigen-specific antibody, where the EMT signature antigen bound by said antibody comprises or is otherwise derived from a protein encoded by: COL11A1, THBS2, COL5A2, COL5A1, VCAN, COL1A1, COL3A1, FN1, SULF1, FBN1, ASPN, SPARC, CTSK, MMP2, BGN, LUM, LOXL2, COL6A3, TIMP3, CDH11, SERPINF1, EDNRA, ACTA2, PDGFRB, SNAI2, LGALS1, GLT8D2, NID2, PRRX1, or VIM. In certain embodiments, the method further comprises a step of detecting FABP4 expression, wherein altered FABP4 expression, i.e., either an increase or decrease in. FABP4 expression, is indicative of EMT. In non-limiting specific embodiments, in a panel provided in said kit, antigens listed above represent up to about 20 percent, or up to about 30 percent, or up to about 50 percent, or up to about 75 percent, or up to about 90 percent, or up to about 100 percent, of the antigens in the entire panel to be tested. Said kit may optionally further comprise one or more positive and/or one or more negative control sample(s).

In certain embodiments, the present invention is directed to kits comprising: (a) a nucleic acid capable of hybridizing to an EMT signature nucleic acid; (b) a control or calibrator reagent; and (c) instructions describing the manner of utilizing the kit. In certain of such embodiments, the kits comprise: (a) a nucleic acid sequence comprising: (i) a target-specific sequence that hybridizes specifically to an EMT signature nucleic acid, and (ii) a detectable label; (b) a primer nucleic acid sequence; (c) a nucleic acid indicator of amplification; and (d) instructions describing the manner of utilizing the kit. In certain of such embodiments, the present invention is directed to kits comprises a nucleic acid that hybridizes specifically to an EMT signature nucleic acid comprising or otherwise derived from: COL11A1, THBS2, COL5A2, COL5A1, VCAN, COL1A1, COL3A1, FN1, SULF1, FBN1, ASPN, SPARC, CTSK, MMP2, BGN, LUM, LOXL2, COL6A3, TIMP3, CDH11, SERPINF1, EDNRA, ACTA2, PDGFRB, SNAI2, LGALS1, GLT8D2, NID2, PRRX1, or VIM. In certain embodiments, the method further comprises a step of detecting FABP4 expression, wherein altered FABP4 expression, i.e., either an increase or decrease in FABP4 expression, is indicative of EMT. In non-limiting specific embodiments, in a panel provided in said kit, EMT signature nucleic acids listed above represent up to about 20 percent, or up to about 30 percent, or up to about 50 percent, or up to about 75 percent, or up to about 90 percent, or up to about 100 percent, of nucleic acids in the entire panel to be tested. Said kit may optionally further comprise one or more positive and/or one or more negative control sample(s).

In certain embodiments, the present invention relates to methods for inhibiting a mesenchymal transition in cell comprising: modulating the expression or activity in said cell of one or more microRNAs selected from the group consisting of miR-214, miR-199a, miR-199b, miR-409, miR-134, miR-200a, miR-200b, and miR-192; and thereby inhibiting a mesenchymal transition in said cell. In certain embodiments, the expression or activity of one or more of miR-214, miR-199a, miR-199b, miR-409, and miR-134 is/are independently or coordinately reduced. In certain embodiments, the expression or activity of one or more of miR-200a, miR-200b, and miR-192 is/are independently or coordinately increased. In certain embodiments, the expression or activity of one or more of miR-214, miR-199a, and miR-199b, is/are independently or coordinately reduced.

In certain embodiments, the present invention relates to methods for inhibition of a cancers cell acquiring a resistance to therapy or increased likelihood of recurrence as the cancer cell acquires properties of stem cells comprising: modulating the expression or activity in said cell of one or more microRNAs selected from the group consisting of miR-214, miR-199a, miR-199b, miR-409, miR-134, miR-200a, miR-200b, and miR-192; and thereby inhibiting the acquisition of resistance to therapy or increased likelihood of recurrence as the cancer cell acquires properties of stem cells in said cancer cell. In certain embodiments, the expression or activity of one or more of miR-214, miR-199a, miR-199b, miR-409, and miR-134 is/are independently or coordinately reduced. In certain embodiments, the expression or activity of one or more of miR-200a, miR-200b, and miR-192 is/are independently or coordinately increased. In certain embodiments, the expression or activity of one or more of miR-214, miR-199a, and miR-199b, is/are independently or coordinately reduced.

In certain embodiments, the present invention relates to methods for inhibition of a cancer cell acquiring an invasive phenotype comprising: modulating the expression or activity in said cell of one or more microRNAs selected from the group consisting of miR-214, miR-199a, miR-199b, miR-409, miR-134, miR-200a, miR-200b, and miR-192; and thereby inhibiting the acquisition of an invasive phenotype in said cancer cell. In certain embodiments, the expression or activity of one or more of miR-214, miR-199a, miR-199b, miR-409, and miR-134 is/are independently or coordinately reduced. In certain embodiments, the expression or activity of one or more of miR-200a, miR-200b, and miR-192 is/are independently or coordinately increased. In certain embodiments, the expression or activity of one or more of miR-214, miR-199a, and miR-199b, is/are independently or coordinately reduced.

In certain embodiments, the present invention relates to the above-described methods wherein said reduction comprises administration of: (a) an antisense molecule targeted to said miRNA; (b) an RNAi molecule targeted to said miRNA; or (c) a catalytic RNA molecule targeted to said microRNA.

In certain embodiments, the present invention relates to the above-described methods wherein said increase comprises: (a) direct administration of said miRNA; (b) introduction of a transgene capable of expressing said miRNA; or (c) influencing the expression of the endogenous coding sequence for said miRNA.

In certain embodiments, the present invention relates to the above-described methods wherein the method comprises first performing a diagnostic step to identify the presence or absence of an EMT signature.

In certain embodiments, the present invention relates to the above-described methods wherein the method comprises a subsequent diagnostic step to identify the presence, absence, increase in, and/or reduction in an EMT signature.

In certain embodiments, the present invention relates to the above-described methods wherein the method comprises reducing the expression or activity of one or more of miR-214, miR-199a, miR-199b, miR-409, and miR-134, and increasing the expression or activity of one or more of miR-200a, miR-200b, and miR-192.

In certain embodiments, the present invention relates to the above-described methods wherein where the method comprises coordinately reducing the expression of miR-199a2 and miR-214. In certain embodiments, the coordinated reduction of miR-199a2 and miR-214 comprises administration of an inhibitor of the expression of a transcript comprising both miR-199a2 and miR-214 sequences, such as the non-coding RNA DNM3OS. In certain embodiments, coordinated inhibitor of miR-199a2 and miR-214 is selected from an antisense oligonucleotide, a RNAi molecule, and a catalytic nucleic acid.

4. Description of the Figures

FIGS. 1(A)-(D) depict scatter plots for the coexpression of the EMT inducing transcription factor Slug (SNAI2) with the main signature genes COL11A1 and THBS2, indicating the strong co-expression as well as continuity of the passing of cancer cells through a Slug-based EMT in solid tumors, and the total absence of the co-expression of these genes otherwise. A, B and C, plots from three solid tumor datasets. D, plot from a leukemia dataset.

FIGS. 2(A)-(C) depict scatter plots in human and mouse of the 18 samples for the expression of the EMT inducing transcription factor Slug (SNAI2) in terms of the expression of the main signature genes COL11A1 and THBS2. A, demonstration that this co-expression is present in the xenografted human cells. B, demonstration that this co-expression is absent in the peritumoral mouse cells. C, Bar diagram indicating that other EMT inducing transcription factors are not co-expressed.

Figure 3:
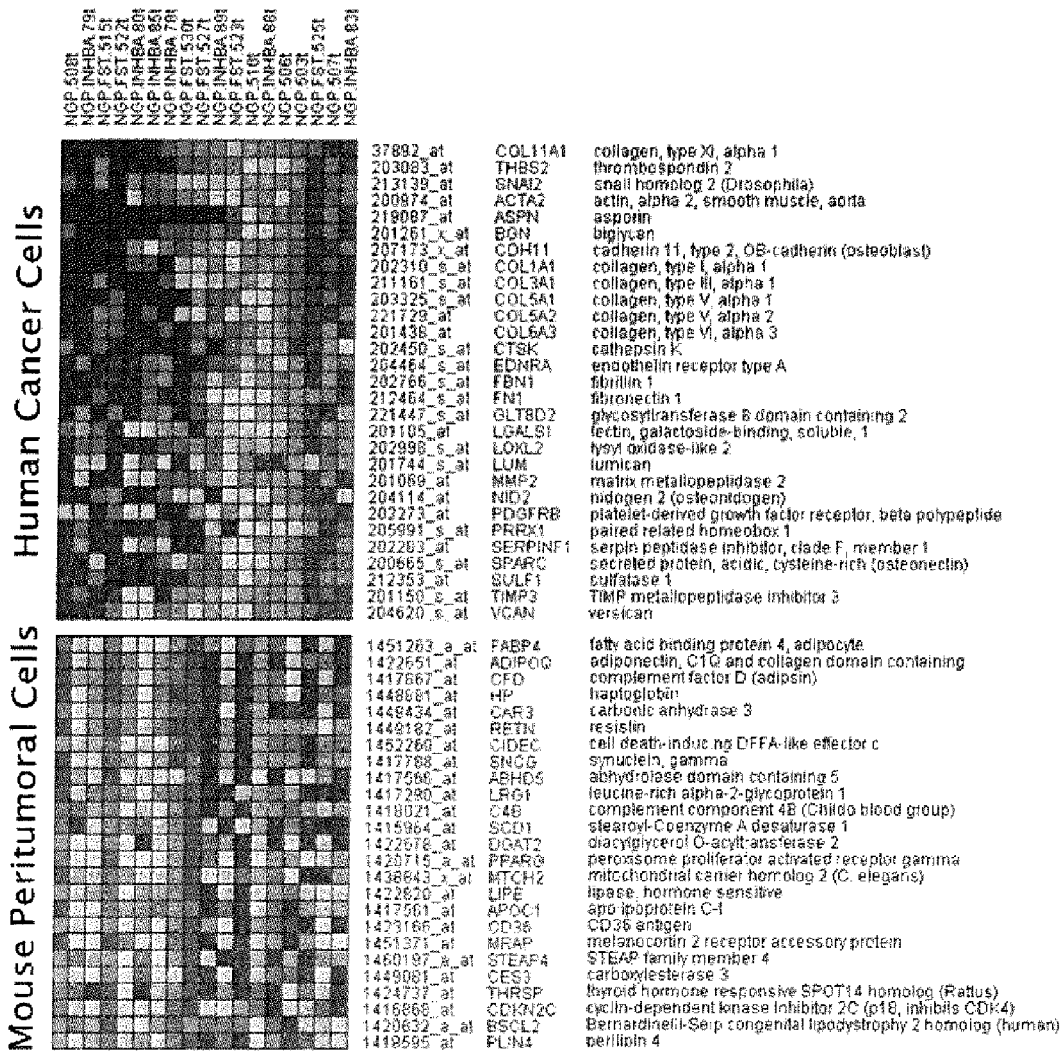

FIG. 3 depicts a heat map combining human and mouse genes. The 29 human genes include many EMT factors and were found to be significantly co-expressed in the cancer cells.

5. Detailed Description of the Invention

5.1. Identification of a Multi-Gene EMT Signature

A precise multi-cancer gene expression signature involving a set of many genes that are coordinately overexpressed only in malignant samples that have exceeded a particular staging threshold, specific to each cancer type, was recently identified and reported. (Kim H, Watkinson J, Varadan V, Anastassiou D (2010) BMC Med Genomics 3: 51). The signature was discovered using computational analysis on numerous publicly available datasets from multiple cancer types, and it was found in all solid cancer types investigated. Among the overexpressed genes are various collagens and proteinases, α-SMA, fibronectin, fibroblast activation protein, and many extracellular matrix glycoproteins, suggesting a fibroblastic source. The signature, however, is not of a general fibroblastic nature, but rather has its own special characteristics, one of which is that genes COL11A1 and THBS2 have a prominent presence in all cases, and they are strongly co-expressed with a remarkably smooth continuous transition. Collagen COL11A1 has been identified as a reliable proxy for the signature. In fact, in each rich solid cancer dataset, but not in non-cancer datasets, finding the list of genes whose expression is most correlated with that of COL11A1 consistently identifies the other genes of the signature. The signature prominently contains only one of the known EMT inducing transcription factors, Slug (SNAI2). Furthermore, the signature contains numerous other EMT-associated genes. The universality of this signature in all solid invasive cancers has recently been further computationally validated (Anastassiou, Available from Nature Precedings <http://precedings.nature.com/documents/6862/version/1>. Indeed, input of the gene set comprising the signature for Gene Set Enrichment Analysis identifies, with "zero" P value, many cancer sets of types (such as nasopharyngeal, lymphomas, head and neck, bladder) that did not participate, in any way whatsoever, in the derivation of the signature. This remarkable validation of the signature by pointing to all kinds of cancer types suggests that the signature reflects a universal biological mechanism present in the invasive stage of all solid cancers.

Although the previously-identified signature includes numerous EMT-associated genes expressed by cancer cells, it also includes genes that are not specifically expressed by cancer cells but which are expressed by other cells in the biopsy sample located in the adjacent microenvironment which participate in the EMT-inducing mechanism by interacting with the cancer cells. While a signature that takes into consideration the expression patterns of all cells obtained via a biopsy or other sampling technique can offer valuable information, a distinct signature that focuses specifically on the expression of cells undergoing an EMT, including, but not limited to, a cancer cells-specific EMT signature, is also useful as described herein.

Many among the genes of the signature were found expressed by the cancer cells themselves in xenografts (Anastassiou et al., BMC Cancer, 11:529 (2011)). The presence of SNAI2 and other EMT marker genes, together with the signature genes COL11A1 and THBS2, among the 29 significantly overexpressed genes in the xenografted human cancer cells demonstrate that cancer cells themselves undergo SNAI2-based EMT and express COL11A1 and THBS2 in solid tumors. Indeed, in solid tumors, identifying the genes whose expression is most correlated with that of COL11A1 consistently reveals the other genes of the signature, including SNAI2. Although this is not observed for healthy samples or nonsolid tumors such as leukemia, such samples can still undergo some form of early or partial SNAI2-based EMT as outlined below.

Furthermore, a subset of the co-expressed genes of the signature, consisting mainly of genes SNAI2, LUM, DCN, COL1A1, COL3A1 and COL6A3 was found also coexpressed even in normal samples in a tissue-specific manner (Cheng and Anastassiou, available from Nature Precedings <http://precedings.nature.com/documents/6813/version/1>, suggesting that a non-fibroblastic version of the same SNAI2-based EMT comprises a general biological mechanism or early or partial EMT that is not necessarily related to cancer, but it still induces cells with properties of stem cells. The genes LUM, DCN, COL1A1, COL3A1 and COL6A3 were identified as consistently strongly co-expressed with SNAI2 in all such cases, including the human body index GEO dataset GSE7307 and the TCGA leukemia and glioblastoma datasets. These genes are also among the genes that are co-expressed with SNAI2, COL11A1, THBS2 and INHBA in solid tumors, consistent with the hypothesis that this is a partial non-fibroblastic EMT signature, while the full fibroblastic EMT signature, including COL11A1 and THBS2, is probably triggered when cancer cells encounter adipocytes in solid cancers (Anastassiou et al., BMC Cancer, 11:529 (2011)).

The above findings indicate that there is an early, or partial, form of SNAI2-based EMT, which is not necessarily associated with cancer, but which can still play an important role when present in cancer, because the presence of an EMT, even in early or partial form, indicates that cells have acquired stem-like properties (Mani et al, Cell, 133, 704-715, 2008), and therefore can be resistant to therapy and/or more likely to cause recurrence following treatment and inducing the surviving cancer cells to evolve into aggressive invasive tumors. Therefore, the decision as to which therapy can be used can be influenced by the presence of even a partial EMT. Furthermore, any therapeutic intervention that inhibits even this early or partial EMT can render additional traditional therapies more effective. Thus, the expression of genes SNAI2, LUM, DCN, COL1A1, COL3A1, COL6A3, even in the absence of expression of the key genes COL11A1, THBS2, INHBA of the complete fibroblastic EMT signature, can serve as important biomarkers for (at least the early or partial form of) the SNAI2-based EMT by themselves.

There are two additional pieces of evidence that the above SNAI2-based EMT, even in its partial form, induces cells with properties of stem cells: First, the corresponding signature was found strongly associated with time to recurrence in glioblastoma (Cheng et al, Available from Nature Precedings <hdl.handle.net/10101/npre.2011.6544.1>2011). Specifically, all glioblastoma patients with exceptionally long time to recurrence following treatment had exceptionally low levels of the signature. This is consistent with the hypothesized reduced stemness in the malignant cells of those patients. Second, the partial SNAI2-based EMT signature was found to be expressed in normal tissues (Cheng et al, Available from Nature Precedings <hdl.handle.net/10101/npre.2012.6813.1>, 2012) in a tissue-specific manner: At one extreme, brain samples do not express the signature at all. At the other extreme, reproductive system samples do. This is consistent with the notion that stemness is prominent in some cells of the reproductive system and least prominent in the highly differentiated cells of the brain. This lack of stemness in normal brain cells is also consistent with the above-mentioned association with prolonged time to recurrence in glioblastoma.

5.2. Assays Employing the EMT Signature

A direct clinical application of the findings described herein concerns the development of high-specificity invasion and/or metastasis-sensing biomarker assay methods. In certain embodiments, such assay methods include, but are not limited: to, nucleic acid amplification assays; nucleic acid hybridization assays; and protein detection assays. In certain embodiments, the assays of the present invention involve combinations of such detection techniques, e.g., but not limited to: assays that employ both amplification and hybridization to detect a change in the expression, such as overexpression or decreased expression, of a gene at the nucleic acid level; immunoassays that detect a change in the expression of a gene at the protein level; as well as combination assays comprising a nucleic acid-based detection step and a protein-based detection step.

"Overexpression", as used herein, refers to an increase in expression of a gene product relative to a normal or control value, which, in non-limiting embodiments, is an increase of at least about 30% or at least about 40% or at least about 50%, or at least about 100%, or at least about 200%, or at least about 300%, or at least about 400%, or at least about 500%, or at least 1000%.

"Decreased expression", as used herein, refers to an decrease in expression of a gene product relative to a normal or control value, which, in non-limiting embodiments, is an decrease of at least about 30% or at least about 40% or at least about 50%, at least about 90%, or a decrease to a level where the expression is essentially undetectable using conventional methods.

As used herein, a "gene product" refers to any product of transcription and/or translation of a gene. Accordingly, gene products include, but are not limited to, pre-mRNA, mRNA, and proteins.

In certain embodiments, the present invention provides compositions and methods for the detection of gene expression indicative of all or part of the EMT signature in a sample using nucleic acid hybridization and/or amplification-based assays.

In non-limiting embodiments, the genes/proteins within the EMT signature set forth above constitute at least 10 percent, or at least 20 percent, or at least 30 percent, or at least 40 percent, or at least 50 percent, or at least 60 percent, or at least 70 percent, or at least 80 percent, or at least 90 percent, of the genes/proteins being evaluated in a given assay.

In certain embodiments, the present invention provides compositions and methods for the detection of gene expression indicative of all or part of the EMT signature in a sample using a nucleic acid hybridization assay, wherein nucleic acid from said sample, or amplification products thereof, are hybridized to an array of one or more nucleic acid probe sequences. In certain embodiments, an "array" comprises a support, preferably solid, with one or more nucleic acid probes attached to the support. Preferred arrays typically comprise a plurality of different nucleic acid probes that are coupled to a surface of a substrate in different, known locations. These arrays, also described as "microarrays" or "chips" have been generally described in the art, for example, U.S. Pat. Nos. 5,143,854, 5,445,934, 5,744,305, 5,677,195, 5,800,992, 6,040,193, 5,424,186 and Fodor et al., Science, 251:767-777 (1991).

Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. See U.S. Pat. Nos. 5,770,358, 5,789,162, 5,708,153, 6,040,193 and 5,800,992.

In certain embodiments, the arrays of the present invention can be packaged in such a manner as to allow for diagnostic, prognostic, and/or predictive use or can be an all-inclusive device; e.g., U.S. Pat. Nos. 5,856,174 and 5,922,591.

In certain embodiments, the hybridization assays of the present invention comprise a primer extension step. Methods for extension of primers from solid supports have been disclosed, for example, in U.S. Pat. Nos. 5,547,839 and 6,770,751. In addition, methods for genotyping a sample using primer extension have been disclosed, for example, in U.S. Pat. Nos. 5,888,819 and 5,981,176.

In certain embodiments, the methods for detection of all or a part of the EMT signature in a sample involves a nucleic acid amplification-based assay. In certain embodiments, such assays include, but are not limited to: real-time PCR (for example see Mackay, Clin. Microbiol. Infect. 10(3): 190-212, 2004), Strand Displacement Amplification (SDA) (for example see Jolley and Nasir, Comb. Chem. High Throughput Screen. 6(3):235-44, 2003), self-sustained sequence replication reaction (3SR) (for example see Mueller et al., Histochem. Cell. Biol. 108(4-5):431-7, 1997), ligase chain reaction (LCR) (for example see Laffler et al., Ann. Biol. Clin. (Paris).51(9):821-6, 1993), transcription mediated amplification (TMA) (for example see Prince et al., J. Viral Hepat. 11(3):236-42, 2004), or nucleic acid sequence based amplification (NASBA) (for example see Romano et al., Clin. Lab. Med. 16(1):89-103, 1996).

In certain embodiments of the present invention, a PCR-based assay, such as, but not limited to, real time PCR is used to detect the presence of an EMT signature in a test sample. In certain embodiments, EMT signature-specific PCR primer sets are used to amplify EMT signature associated RNA and/or DNA targets. Signal for such targets can be generated, for example, with fluorescence-labeled probes. In the absence of such target sequences, the fluorescence emission of the fluorophore can be, in certain embodiments, eliminated by a quenching molecule also operably linked to the probe nucleic acid. However, in the presence of the target sequences, probe binds to template strand during primer extension step and the nuclease activity of the polymerase catalyzing the primer extension step results in the release of the fluorophore and production of a detectable signal as the fluorophore is no longer linked to the quenching molecule. (Reviewed in Bustin, J. Mol. Endocrinol. 25, 169-193 (2000)). The choice of fluorophore (e.g., FAM, TET, or Cy5) and corresponding quenching molecule (e.g. BHQ1 or BHQ2) is well within the skill of one in the art and specific labeling kits are commercially available.

In certain embodiments, the present invention provides compositions and methods for the detection of gene expression indicative of all or part of the EMT signature in a sample by employing high throughput sequencing techniques, such as RNA-seq. (See, e.g., Wang et al., RNA-Seq: a revolutionary tool for transcriptomics, Nat Rev Genet. 2009 January; 10(1): 57-63). In general, such techniques involve obtaining a sample population of RNA (total or fractionated, such as poly(A)+) which is then converted to a library of cDNA fragments, typically of 30-400 bp in length. These cDNA fragments will be generated to include adaptors attached to one or both ends, depending on whether the subsequent sequencing step proceeds from one or both ends. Each of the adaptor-tagged molecules, with or without amplification, can then be sequenced in a high-throughput manner to obtain short sequences. Virtually any high-throughput sequencing technology can be used for the sequencing step, including, but not limited to the Illumina IG®, Applied Biosystems SOLiD®, Roche 454 Life Science, and Helicos Biosciences tSMS® systems. Following sequencing, bioinfoimatics techniques can be used to either align there results against a reference genome or to assemble the results de novo. Such analysis is capable of identifying both the level of expression for each gene as well as the sequence of particular expressed genes.

In certain embodiments, the present invention provides compositions and methods for the detection of gene expression indicative of all or part of the EMT signature in a sample by detecting changes in concentration of the protein, or proteins, encoded by the genes of interest.

In certain embodiments, the present invention relates to the use of immunoassays to detect modulation of gene expression by detecting changes in the concentration of proteins expressed by a gene of interest. Numerous techniques are known in the art for detecting changes in protein expression via immunoassays. (See The Immunoassay Handbook, 2nd Edition, edited by David Wild, Nature Publishing Group, London 2001.) In certain of such immunoassays, antibody reagents capable of specifically interacting with a protein of interest, e.g., an individual member of the EMT signature, are covalently or non-covalently attached to a solid phase. Linking agents for covalent attachment are known and may be part of the solid phase or derivatized to it prior to coating. Examples of solid phases used in immunoassays are porous and non-porous materials, latex particles, magnetic particles, microparticles, strips, beads, membranes, microtiter wells and plastic tubes. The choice of solid phase material and method of labeling the antibody reagent are determined based upon desired assay format performance characteristics. For some immunoassays, no label is required, however in certain embodiments, the antibody reagent used in an immunoassay is attached to a signal-generating compound or "label". This signal-generating compound or "label" is in itself detectable or may be reacted with one or more additional compounds to generate a detectable product (see also U.S. Pat. No. 6,395,472 B1). Examples of such signal generating compounds include chromogens, radioisotopes (e.g., $^{125}$I, $^{131}$I, $^{32}$P, $^3$H, $^{35}$S, and $^{14}$C), fluorescent compounds (e.g., fluorescein and rhodamine), chemiluminescent compounds, particles (visible or fluorescent), nucleic acids, complexing agents, or catalysts such as enzymes (e.g., alkaline phosphatase, acid phosphatase, horseradish peroxidase, beta-galactosidase, and ribonuclease). In the case of enzyme use, addition of chromo-, fluoro-, or lumo-genic substrate results in generation of a detectable signal. Other detection systems such as time-resolved fluorescence, internal-reflection fluorescence, amplification (e.g., polymerase chain reaction) and Raman spectroscopy are also useful in the context of the methods of the present invention.

A "sample" from a subject to be tested according to one of the assay methods described herein may be at least a portion of a tissue, at least a portion of a tumor, a cell, a collection of cells, or a fluid (e.g., blood, cerebrospinal fluid, urine, expressed prostatic fluid, peritoneal fluid, a pleural effusion, peritoneal fluid, etc.). In certain embodiments the sample used in connection with the assays of the instant invention will be obtained via a biopsy. Biopsy may be done by an open or percutaneous technique. Open biopsy is conventionally performed with a scalpel and can involve removal of the entire tumor mass (excisional biopsy) or a part of the tumor mass (incisional biopsy). Percutaneous biopsy, in contrast, is commonly performed with a needle-like instrument either blindly or with the aid of an imaging device, and may be either a fine needle aspiration (FNA) or a core biopsy. In FNA biopsy, individual cells or clusters of cells are obtained for cytologic examination. In core biopsy, a core or fragment of tissue is obtained for histologic examination which may be done via a frozen section or paraffin section.

In certain embodiments of the present invention, the assay methods described herein can be employed to detect the presence of the EMT signature in cancer and non-cancer cells. In certain embodiments of the present invention, the assay methods described herein can be employed to detect the presence of the EMT signature in cancer. In certain embodiments, such cancers can include those involving the presence of solid tumors. In certain embodiments such cancers can include epithelial cancers. In certain embodiments such cancers can include non-epithelial cancers. In certain embodiments, such epithelial and non-epithelial cancers can include, for example, but not by way of limitation, cancers of the ovary, stomach, pancreas, duodenum, liver, colon, breast, vagina, cervix, prostate, lung, testicle, oral cavity, esophagus, as well as neuroblastoma and Ewing's sarcoma.

In certain embodiments, the present invention is directed to assay methods allowing for diagnostic, prognostic, and/or predictive use of the EMT signature. For example, but not by way of limitation, the assay methods described herein can be used in a diagnostic context, e.g., where a cell undergoing an EMT can be identified or where invasive cancer can be diagnosed by detecting all or part of the EMT signature in a sample. In certain non-limiting embodiments, the assay methods described herein can be used in a prognostic context, e.g., where detection of all or part of the EMT signature allows for an assessment of the likelihood of future EMT or future metastasis, including in those situations where such metastasis is not yet identified. In certain non-limiting embodiments, the assay methods described herein can be used in predictive context, e.g., where detection of all or part of the EMT signature allows for an assessment of the likely benefit of certain types of therapy, such as, but not limited to, neoadjuvant therapy, surgical resection, and/or chemotherapy.

In certain non-limiting embodiments, the markers and assay methods of the present invention can be used to determine whether a cancer in a subject has progressed to a invasive and/or metastatic form, or has remitted (for example, in response to treatment).

In certain non-limiting embodiments, the markers and assay methods of the present invention can be used to stage a cancer (where clinical staging considers whether invasion has occurred). Such multi-cancer staging is possible due to the fact that the EMT signature is present in a variety of cancers as a marker of invasion and the acquisition of such invasive quality correlates with the cancer having achieved a particular stage. For example, but not by way of limitation, the markers and assay methods of the present invention can be used to identify when breast carcinoma in situ becomes invasive, which correlates with the carcinoma achieving stage I. In alternative embodiments, the markers and assay methods of the present invention can be used to identify when ovarian cancer becomes invasive, which correlates with the cancer achieving stage III, and more particularly, stage IIIc. In alternative embodiments, the markers and assay methods of the present invention can be used to identify when colorectal cancer becomes invasive, which correlates with the cancer achieving stage II. In alternative embodiments, the markers and assay methods of the present invention can be used to identify when a neuroblastoma becomes invasive, which correlates with the neuroblastoma having progressed beyond stage I.

In certain non-limiting embodiments, the EMT signature, or a subset of markers associated with it, can be used to evaluate the contextual (relative) benefit of a therapy in a subject. For example, if a therapeutic decision is based on an assumption that a cancer is localized in a subject, the presence of the EMT signature, or a subset of markers associated with it, would suggest that the cancer is invasive. As a specific, non-limiting embodiment, the relative benefit, to a subject with a malignant tumor, of neoadjuvant chemo- and/or immuno-therapy prior to surgical or radiologic anti-tumor treatment can be assessed by determining the presence of the EMT signature or a subset of markers associated with it, where the presence of the EMT signature or a subset of markers associated with it, is indicative of a decrease in the relative benefit conferred by the neoadjuvant therapy to the subject.

In certain embodiments, the assays of the present invention are capable of detecting coordinated modulation of expression, for example, but not limited to, overexpression, of the genes associated with the EMT signature. In certain embodiments, such detection involves, but is not limited to, detection of the expression of SNAI2, LUM, and DCN. In certain embodiments, such detection involves, but is not limited to, detection of the expression of at least one of, at least two of, at least three of, at least four of, or at least five, at least six, or at least all seven of the following proteins: SNAI2, LUM, DCN, COL1A1, COL1A2, COL3A1, and COL6A3. In certain embodiments, the method further comprises a step of detecting FABP4 expression, wherein altered FABP4 expression, i.e., either an increase or decrease in FABP4 expression, is indicative of EMT.

In certain embodiment, a sample from a subject either diagnosed with a cancer or who is being evaluated for the presence or stage of cancer (where the cancer is preferably, but is not limited to, an epithelial cancer) may be tested for the presence of EMT genes and/or overexpression of at least one of, at least two of, at least three of, at least four of, or at least five, at least six, or at least all seven of the following: SNAI2, LUM, DCN, COL1A1, COL1A2, COL3A1, and COL6A3; as well as one or more or two or more or three or more of the following: COL11A1, THBS2, COL5A2, COL5A1, VCAN, FN1, SULF1, FBN1, ASPN, SPARC, CTSK, MMP2, BGN, LOXL2, TIMP3, CDH11, SERPINF1, EDNRA, ACTA2, PDGFRB, LGALS1, GLT8D2, NID2, PRRX1, and VIM. Preferably but without limitation SNAI1 expression is not altered (in addition, in certain non-limiting embodiments, the SNAI1 gene is methylated). In one specific non-limiting embodiment of the invention, overexpression of at least one of, at least two of, at least three of at least four of, or at least five, at least six, or at least all seven of the following proteins: SNAI2, LUM, DCN, COL1A1, COL1A2, COL3A1, and COL6A3, but not SNAI1 is indicative of a diagnosis of cancer having invasive and/or metastatic progression. In certain embodiments, the method further comprises a step of detecting FABP4 expression, wherein altered FABP4 expression, i.e., either an increase or decrease in FABP4 expression, is indicative of EMT.

In certain embodiments, a high-specificity invasion-sensing biomarker assay of the present invention detects overexpression of SNAI2.

In certain embodiments, the high-specificity invasion-sensing biomarker assay detects coordinated overexpression of SNAI2, LUM, and DCN. In certain embodiments the high-specificity invasion-sensing biomarker assay detects coordinated overexpression of SNAI2, LUM, DCN, COL1A1, COL1A2, COL3A1, and COL6A3.

In certain embodiments, the high-specificity invasion-sensing biomarker assay detects coordinated overexpression of at least one of, at least two of, at least three of at least four of, or at least five, at least six, or at least all seven of the following proteins: SNAI2, LUM, DCN, COL1A1, COL1A2, COL3A1, and COL6A3, but not SNAI1; as well as one or more or two or more or three or more of the following: COL11A1, THBS2, COL5A2, COL5A1, VCAN, FN1, SULF1, FBN1, ASPN, SPARC, CTSK, MMP2, BGN, LOXL2, TIMP3, CDH11, SERPINF1, EDNRA, ACTA2, PDGFRB, LGALS1, GLT8D2, NID2, PRRX1, and VIM.

In certain embodiments, the high-specificity invasion-sensing biomarker assay detects coordinated overexpression of at least one of, at least two of, at least three of, at least four of or at least five, at least six, or at least all seven of the following proteins: SNAI2, LUM, DCN, COL1A1, COL1A2, COL3A1, and COL6A3, in combination with differential expression of one or more microRNAs selected from the group consisting of: miR-214, miR-199a, and miR-199b.

In certain embodiments, the high-specificity invasion-sensing biomarker assay detects coordinated overexpression of at least one of, at least two of, at least three of, at least four of, or at least five, at least six, or at least all seven of the following proteins: SNAI2, LUM, DCN, COL1A1, COL1A2, COL3A1, and COL6A3, in combination with differential expression of one or more microRNAs selected from the group consisting of: hsa-miR-22; hsa-miR-514-1/hsa-miR-514-2|hsa-miR-514-3; hsa-miR-152; hsa-miR-508; hsa-miR-509-1/hsa-miR-509-2/hsa-miR-509-3; hsa-miR-507; hsa-miR-509-1/hsa-miR-509-2; hsa-miR-506; hsa-miR-509-3; hsa-miR-214; hsa-miR-510; hsa-miR-199a-1/hsa-miR199a-2; hsa-miR-21; hsa-miR-513c; and hsa-miR-199b.

Diagnostic kits are also included within the scope of the present invention. More specifically, the present invention includes kits for determining the presence of all or a portion of the EMT signature in a test sample.

Kits directed to determining the presence of all or a portion of the EMT signature in a sample may comprise: a) at least one EMT signature antigen comprising an amino acid sequence selected from the group consisting of) and b) a conjugate comprising an antibody that specifically interacts with said EMT signature antigen attached to a signal-generating compound capable of generating a detectable signal. The kit can also contain a control or calibrator that comprises a reagent which binds to the antigen as well as an instruction sheet describing the manner of utilizing the kit.

In certain embodiments, the present invention is directed to kits comprising: (a) a conjugate comprising an antibody that specifically interacts with an EMT signature antigen attached to a signal-generating compound capable of generating a detectable signal; (b) a control or calibrator reagent, and (c) instructions describing the manner of utilizing the kit. In certain of such embodiments, the present invention is directed to kits comprising: a EMT signature antigen-specific antibody, where the EMT signature antigen bound by said antibody comprises or is otherwise derived from a protein encoded by SNAI2, LUM, DCN, COL1A1, COL1A2, COL3A1, or COL6A3. In certain embodiments, the method further comprises a step of detecting FABP4 expression, wherein altered FABP4 expression, i.e., either an increase or decrease in FABP4 expression, is indicative of EMT. In non-limiting specific embodiments, in a panel provided in said kit, antigens listed above represent up to about 20 percent, or up to about 30 percent, or up to about 50 percent, or up to about 75 percent, or up to about 90 percent, or up to about 100 percent, of the antigens in the entire panel to be tested. Said kit may optionally further comprise one or more positive and/or one or more negative control sample(s).

In certain embodiments, the present invention is directed to kits comprising: (a) a nucleic acid capable of hybridizing to an EMT signature nucleic acid; (b) a control or calibrator reagent; and (c) instructions describing the manner of utilizing the kit. In certain of such embodiments, the kits comprise: (a) a nucleic acid sequence comprising: (i) a target-specific sequence that hybridizes specifically to an EMT signature nucleic acid, and (ii) a detectable label; (b) a primer nucleic acid sequence; (c) a nucleic acid indicator of amplification; and. (d) instructions describing the manner of utilizing the kit. In certain of such embodiments, the present invention is directed to kits comprising a nucleic acid that hybridizes specifically to an EMT signature nucleic acid comprising or otherwise derived from of at least one of, at least two of, at least three of, at least four of or at least five, at least six, or at least all seven of the following: SNAI2, LUM, DCN, COL1A1, COL1A2, COL3A1, and COL6A3. In certain embodiments, the method further comprises a step of detecting FABP4 expression, wherein altered FABP4 expression, i.e., either an increase or decrease in FABP4 expression, is indicative of EMT. In non-limiting specific embodiments, in a panel provided in said kit, EMT signature nucleic acids listed above represent up to about 20 percent, or up to about 30 percent, or up to about 50 percent, or up to about 75 percent, or up to about 90 percent, or up to about 100 percent, of nucleic acids in the entire panel to be tested. Said kit may optionally further comprise one or more positive and/or one or more negative control sample(s).

In certain embodiments, the present invention is directed to kits comprising: (a) a conjugate comprising an antibody that specifically interacts with an EMT signature antigen attached to a signal-generating compound capable of generating a detectable signal; (b) a control or calibrator reagent, and (c) instructions describing the manner of utilizing the kit. In certain of such embodiments, the present invention is directed to kits comprising: a EMT signature antigen-specific antibody, where the EMT signature antigen bound by said antibody comprises or is otherwise derived from a protein encoded by: COL11A1, THBS2, COL5A2, COL5A1, VCAN, COL1A1, COL3A1, FN1, SULF1, FBN1, ASPN, SPARC, CTSK, MMP2, BGN, LUM, LOXL2, COL6A3, TIMP3, CDH11, SERPINF1, EDNRA, ACTA2, PDGFRB, SNAI2, LGALS1, GLT8D2, NID2, PRRX1, or VIM. In certain embodiments, the method further comprises a step of detecting FABP4 expression, wherein altered FABP4 expression, i.e., either an increase or decrease in FABP4 expression, is indicative of EMT. In non-limiting specific embodiments, in a panel provided in said kit, antigens listed above represent up to about 20 percent, or up to about 30 percent, or up to about 50 percent, or up to about 75 percent, or up to about 90 percent, or up to about 100 percent, of the antigens in the entire panel to be tested. Said kit may optionally further comprise one or more positive and/or one or more negative control sample(s).

In certain embodiments, the present invention is directed to kits comprising: (a) a nucleic acid capable of hybridizing to an EMT signature nucleic acid; (b) a control or calibrator reagent; and (c) instructions describing the manner of utilizing the kit. In certain of such embodiments, the kits comprise: (a) a nucleic acid sequence comprising: (i) a target-specific sequence that hybridizes specifically to an EMT signature nucleic acid, and (ii) a detectable label; (b) a primer nucleic acid sequence; (c) a nucleic acid indicator of amplification; and (d) instructions describing the manner of utilizing the kit. In certain of such embodiments, the present invention is directed to kits comprises a nucleic acid that hybridizes specifically to an EMT signature nucleic acid comprising or otherwise derived from: COL11A1, THBS2, COL5A2, COL5A1, VCAN, COL1A1, COL3A1, FN1, SULF1, FBN1, ASPN, SPARC, CTSK, MMP2, BGN, LUM, LOXL2, COL6A3, TIMP3, CDH11, SERPINF1, EDNRA, ACTA2, PDGFRB, SNAI2, LGALS1, GLT8D2, NID2, PRRX1, or VIM. In certain embodiments, the method further comprises a step of detecting FABP4 expression, wherein altered FABP4 expression, i.e., either an increase or decrease in FABP4 expression, is indicative of EMT. In non-limiting specific embodiments, in a panel provided in said kit, EMT signature nucleic acids listed above represent up to about 20 percent, or up to about 30 percent, or up to about 50 percent, or up to about 75 percent, or up to about 90 percent, or up to about 100 percent, of nucleic acids in the entire panel to be tested. Said kit may optionally further comprise one or more positive and/or one or more negative control sample(s).

In certain embodiments, the hybridization and/or nucleic acid amplification assays that can be employed using the kits of the present invention include, but are not limited to: real-time PCR (for example see Mackay, Clin. Microbiol. Infect. 10(3):190-212, 2004), Strand Displacement Amplification (SDA) (for example see Jolley and Nasir, Comb. Chem. High Throughput Screen. 6(3):235-44, 2003), self-sustained sequence replication reaction (3SR) (for example see Mueller et al., Histochem. Cell. Biol. 108(4-5):431-7, 1997), ligase chain reaction (LCR) (for example see Laffler et al., Ann. Biol. Clin. Paris).51(9):821-6, 1993), transcription mediated amplification (TMA) (for example see Prince et al., J. Viral Hepat. 11(3):236-42, 2004), or nucleic acid sequence based amplification (NASBA) (for example see Romano et al., Clin. Lab. Med. 16(1):89-103, 1996).

In certain embodiments of the present invention, a kit for detection of EMT signature nucleic acids comprises: (1) a nucleic acid sequence comprising a target-specific sequence that hybridizes specifically to an EMT signature nucleic acid target, and (ii) a detectable label. Such kits can further comprise one or more additional nucleic acid sequence that can function as primers, including nested and/or heminested primers, to mediate amplification of the target sequence. In certain embodiments, the kits of the present invention can further comprise additional nucleic acid sequences function as indicators of amplification, such as labeled probes employed in the context of a real time polymerase chain reaction assay.

The kits of the invention are also useful for detecting multiple EMT signature nucleic acids either simultaneously or sequentially. In such situations, the kit can comprise, for each different nucleic acid target, a different set of primers and one or more distinct labels.

In certain embodiments, the kit comprises nucleic acids (e.g., hybridization probes, primers, or RT-PCR probes) individually comprising or otherwise derived from: SNAI2, LUM, DCN, COL1A1, COL1A2, COL3A1, or COL6A3.

Any of the exemplary assay formats described herein and any kit according to the invention can be adapted or optimized for use in automated and semi-automated systems (including those in which there is a solid phase comprising a microparticle), for example as described, e.g., in U.S. Pat. Nos. 5,089,424 and 5,006,309, and in connection with any of the commercially available detection platforms known in the art.

In certain embodiments, the methods, assays, and/or kits of the present invention are directed to the detection of all or a part of the EMT signature wherein such detection can take the form of either a binary, detected/not-detected, result. In certain embodiments, the methods, assays, and/or kits of the present invention are directed to the detection of all or a part of the EMT signature wherein such detection can take the form of a multi-factorial result. For example, but not by way of limitation, such multi-factorial results can take the form of a score based on one, two, three, or more factors. Such factors can include, but are not limited to: (1) detection of a change in expression of an EMT signature gene product, state of methylation, and/or presence of microRNA; (2) the number of EMT signature gene products, states of methylation, and/or presence of microRNAs in a sample exhibiting an altered level; and (3) the extent of such change in EMT signature gene products, states of methylation, and/or presence of microRNAs.

5.3. Methods of Treatment Based on the EMT Signature

5.3.1. Therapeutic Interventions Based on Identification of EMT Signature

In further non-limiting embodiments, the present invention provides for methods of treating a subject, such as, but not limited to, methods comprising performing a diagnostic method as set forth above and then, if an EMT signature is detected in a sample of the subject, recommending that the patient undergo a further diagnostic procedure (e.g. an imaging procedure such as X-ray, ultrasound, computerized axial tomography (CAT scan) or magnetic resonance imaging (MRI)), and/or recommending that the subject be administered therapy with an agent that inhibits invasion and/or metastasis.

In certain non-limiting embodiments of the present invention, a diagnostic method as set forth above is performed and a therapeutic decision is made in light of the results of that assay. For example, but not by way of limitation, a therapeutic decision, such as whether to prescribe neoadjuvant chemo- and/or immunotherapy prior to surgical or radiologic anti-tumor treatment can be made in light of the results of a diagnostic method as set for the above. The results of the diagnostic method are relevant to the therapeutic decision as the presence of the EMT signature or a subset of markers associated with it, in a sample from a subject indicates a decrease in the relative benefit conferred by the neoadjuvant therapy to the subject since the presence of the EMT signature, or a subset of markers associated with it, is indicative of a cancer that is not localized.

In certain embodiments, a diagnostic method as set forth above is performed and a decision regarding whether to continue a particular therapeutic regimen is made in light of the results of that assay. For example, but not by way of limitation, a decision whether to continue a particular therapeutic regimen, such as whether to continue with a particular chemotherapeutic, radiation therapy, and/or molecular targeted therapy (e.g., a cancer cell-specific antibody therapeutic) can be made in light of the results of a diagnostic method as set for the above. The results of the diagnostic method are relevant to the decision whether to continue a particular therapeutic regimen as the presence of the EMT signature or a subset of markers associated with it, in a sample from a subject can be indicative of the subject's responsiveness to that therapeutic.

5.3.2. Therapies Involving EMT-Related microRNAs

The present invention also relates to the discovery that the modulation of particular microRNAs can be employed to inhibit a mesenchymal transition that, in certain instances, correlates with resistance to therapy and recurrence as the corresponding cells acquire properties of stem cells as they start undergoing this transition, as well as with invasiveness, e.g., invasion of certain cells of primary tumors into adjacent connective tissue during the initial phase of metastasis. Accordingly, the identification inhibitors of this mechanism, such as inhibitors of certain microRNAs, disclosed herein, can be used for inhibiting the mesenchymal transition to reduce the invasive nature of certain cells of primary cancerous tumors and, in certain instances, to prevent the recurrence of cancer by inhibiting the induction of stem cell-like features in certain cancer cells.

Certain microRNAs that were previously identified in the complete EMT signature (as being strongly correlated with COL11A1 in solid cancers) were investigated in the presence of additional publicly available cancer datasets, and are shown to correlate with the expression of SNAI2 and the other genes of the signature even in nonsolid cancers. Indeed, the following microRNAs: miR-214, miR-199a, miR-199b, miR-409, and miR-134 were found to be consistently positively co-expressed with the genes of the signature, while miR-200a, miR-200b, and miR-192 were found to be consistently negatively associated with the genes of the signature. These microRNAs can not only serve as biomarkers for, in certain embodiments, the full or partial form of the SNAI2-based EMT by themselves, but also, as disclosed herein, as targets for therapeutic intervention.

MicroRNAs, such as miR-214, miR-199a, miR-199b, miR-409, miR-134 miR-200a, miR-200b, and miR-192 are produced, depending on the specific species of microRNA, from either their own genes or from introns. MicroRNAs are initially transcribed as either a pri-miRNA (when transcribed from their own genes) or as pre-mRNA (when present in an intron of a pre-mRNA molecule). These miRNA-containing molecules are first processed to produce a pre-miRNA hairpin precursor molecule, which is further processed to produce mature microRNA molecules, including the mature microRNA sequences identified in Table 1. As used herein, the term microRNA is intended to encompass pri-miRNA, pre-miRNA, and mature microRNAs, e.g., the term miR-214 is intended to encompass miR-214 in all of its precursor and mature forms, including, but not limited to pre-miR-214, miR-214-5p and miR-214-3p. Thus, therapeutic interventions that modulate the expression and/or activity of microRNAs may exert their effect by modulating the expression and/or activity at any level (e.g., pri-miRNA, pre-miRNA, and/or mature microRNA).

TABLE 1 microRNA Sequences

| microRNA | Sequence |
| --- | --- |
| miR-214-5p | UGCCUGUCUACACUUGCUGUGC (SEQ ID NO: 1) |
| miR-214-3p | ACAGCAGGCACAGACAGGCAGU (SEQ ID NO: 2) |
| miR-199a-5p | CCCAGUGUUCAGACUACCUGUUC (SEQ ID NO: 3) |
| miR-199a-3p | ACAGUAGUCUGCACAUUGGUUA (SEQ ID NO: 4) |
| miR-199b-5p | CCCAGUGUUUAGACUAUCUGUUC (SEQ ID NO: 5) |
| miR-199b-3p | ACAGUAGUCUGCACAUUGGUUA (SEQ ID NO: 6) |
| miR-409-5p | AGGTTACCCGAGCAACTTTGCAT (SEQ ID NO: 7) |
| mir-409-3p | GAATGTTGCTCGGTGAACCCCT (SEQ ID NO: 8) |
| miR-134 | TGTGACTGGTTGACCAGAGGGG (SEQ ID NO: 9) |
| miR-200a-5p | CAUCUUACCGGACAGUGCUGGA (SEQ ID NO: 10) |
| miR-200a-3p | UAACACUGUCUGGUAACGAUGU (SEQ ID NO: 11) |
| miR-200b-5p | CAUCUUACUGGGCAGCAUUGGA (SEQ ID NO: 12) |
| miR-200b-3p | UAAUACUGCCUGGUAAUGAUGA (SEQ ID NO: 13) |
| miR-192-5p | CUGACCUAUGAAUUGACAGCC (SEQ ID NO: 14) |
| miR192-3p | CUGCCAAUUCCAUAGGUCACAG (SEQ ID NO: 15) |

In certain embodiments, the present invention is directed to the inhibition of a mesenchymal transition that correlates with the expression of the EMT signature described herein, wherein such inhibition is achieved by appropriately modulating the expression and/or activity of one or more of the following microRNAs: miR-214, miR-199a, miR-199b, miR-409, miR-134, miR-200a, miR-200b, and miR-192. Specifically, when engaging in such modulation, the expression and/or activity of the following microRNAs would be independently or coordinately reduced: miR-214, miR-199a, miR-199b, miR-409, and miR-134, while the expression and/or activity of the following microRNAs would be independently or coordinately increased: miR-200a, miR-200b, and miR-192. In certain embodiments, such inhibition can be achieved by independently or coordinately reducing the expression and/or activity of miR-214, miR-199a, and miR-199b.

In certain embodiments, the present invention is directed to the inhibition of cancers cells acquiring a resistance to therapy and/or increased likelihood of recurrence as the cancer cells acquire properties of stem cells, where the acquisition of such properties correlates with the expression the EMT signature described herein. For example, but not by way of limitation, such inhibition can be achieved by appropriately modulating the expression and/or activity of one or more of the following microRNAs: miR-214, miR-199a, miR-199b, miR-409, miR-134, miR-200a, miR-200b, and miR-192. Specifically, when engaging in such modulation, the expression and/or activity of the following microRNAs would be independently or coordinately reduced: miR-214, miR-199a, miR-199b, miR-409, and miR-134, while the expression and/or activity of the following microRNAs would be independently or coordinately increased: miR-200a, miR-200b, and miR-192. In certain embodiments, such inhibition can be achieved by independently or coordinately reducing the expression and/or activity of miR-214, miR-199a, and miR-199b.

In certain embodiments, the present invention is directed to the inhibition of invasiveness, e.g., invasion of certain cells of primary tumors into adjacent connective tissue during the initial phase of metastasis, which correlates with the expression of the EMT signature described herein. For example, but not by way of limitation, such inhibition can be achieved by appropriately modulating the expression and/or activity of one or more of the following microRNAs: miR-214, miR-199a, miR-199b, miR-409, miR-134, miR-200a, miR-200b, and miR-192. Specifically, when engaging in such modulation, the expression and/or activity of the following microRNAs would be independently or coordinately reduced: miR-214, miR-199a, miR-199b, miR-409, and miR-134, while the expression and/or activity of the following microRNAs would be independently or coordinately increased: miR-200a, miR-200b, and miR-192. In certain embodiments, such inhibition can be achieved by independently or coordinately reducing the expression and/or activity of miR-214, miR-199a, and miR-199b.

Certain techniques for the modulation of expression and/or activity of microRNAs are well known in the art (see, e.g., Broderick and Zamore, MicroRNA Therapeutics, Gene Therapy, 18, 1104-1110 (2011), which is incorporated herein by reference in its entirety). For example, but not by way of limitation, microRNA expression and/or activity can be reduced by administration of antisense molecules capable of binding to the miRNA of interest and thereby inhibiting the activity of the microRNA. Alternatively, RNAi or catalytic RNA molecules can be designed such that they are capable of specifically binding the microRNA of interest and thereby inducing the destruction of that microRNA. Exemplary techniques for increasing expression and/or activity of microRNAs include, but are not limited to, direct administration of the microRNA of interest, the introduction of a transgene capable of expressing the microRNA of interest, and influencing the expression and/or activity of the endogenous microRNA coding sequence.

Certain embodiments of the present invention comprise coupling one or more of the above-described techniques for modulating microRNA expression and/or activity with an initial diagnostic step whereby the above-described EMT signature is identified. In certain of such embodiments, the technique for modulation microRNA expression and/or activity is followed by one or more subsequent diagnostic steps to monitor an increase or decrease in the presence of the EMT signature. In alternative embodiments, an initial diagnostic step is not performed, and only the one or more subsequent diagnostic steps are performed.

Certain embodiments of the present invention comprise coupling one or more of the above-described techniques for modulating microRNA expression and/or activity with an one or more additional techniques for modulating microRNA expression and/or activity. For example, but not by way of limitation, a techniques for reducing the expression and/or activity for one or more of miR-214, miR-199a, miR-199b, miR-409, and miR-134, can be coupled to a technique for increasing the expression and/or activity of one or more of miR-200a, miR-200b, and miR-192. In addition, such combinations of techniques for modulating the expression and/or activity of the specified microRNAs can be practiced in concert with an initial diagnostic step whereby the above-described EMT signature is identified. In certain of such embodiments, the techniques for modulation microRNA expression and/or activity is followed by one or more subsequent diagnostic steps to monitor an increase or decrease in the presence of the EMT signature. In alternative embodiments, an initial diagnostic step is not performed, and only the one or more subsequent diagnostic steps are performed.

In certain embodiments, the methods of the instant invention will make use of the fact that certain microRNAs are coordinately expressed via their genomic locations. For example, but not by way of limitation, miR-199a2 and miR-214 are located in the same transcript within an intron of a protein coding gene (dynamin-3), while miR-199a1 and miR-199b are located in other genomic regions, but still within introns of the protein coding genes of the dynamin family, although not necessarily on the coding strand (i.e., microRNAs may be present on non-coding, opposite strand, sequences). Furthermore, the miR-199a2/214 cluster has previously been associated with the EMT-inducing transcription factor Twist and these two microRNAs are regulated as a cluster within the human DNM3OS gene (Lee et al, Nucleic Acids Research, 2009 January; 37(1): 123-128, Yin et al, Oncogene, 2010, 29, 3545-3553). In certain embodiments of the present invention, the inhibition of certain microRNAs, e.g., miR-199a2 and miR-214 can be achieved in a coordinated manner by inhibiting the expression and/or activity of the single transcript containing both sequences. In certain of such embodiments such inhibition is achieved via the introduction of antisense, RNAi, and/or catalytic nucleic acid inhibitors of one or more of the dynamin family coding sequences.

In certain embodiments, the present invention relates to methods of inhibiting the expression and/or activity of certain microRNAs, including miR-214, miR-199a, miR-199b, miR-409, and miR-134 using antisense oligonucleotides. For example, in certain embodiments, the miR-214, miR-199a, miR-199b, miR-409, and miR-134 inhibitors are antisense oligonucleotides targeting the mature miR-214, miR-199a, miR-199b, miR-409, and miR-134 sequences. The antisense oligonucleotides can be ribonucleotides or deoxyribonucleotides. In certain embodiments, the antisense oligonucleotides have at least one chemical modification. For instance, suitable antisense oligonucleotides can be comprised of one or more "conformationally constrained" or bicyclic sugar nucleoside modifications, for example, "locked nucleic acids" (LNAs). LNAs are modified ribonucleotides that contain a bridge between the 2' and 4' carbons of the ribose sugar moiety resulting in a "locked"

conformation that confers enhanced thermal stability to oligonucleotides containing the LNAs. In certain embodiments, the antisense oligonucleotides targeting miR-214, miR-199a, miR-199b, miR-409, and miR-134 can contain combinations of LNAs or other modified nucleotides and ribonucleotides or deoxyribonucleotides. Alternatively, the antisense oligonucleotides can comprise peptide nucleic acids (PNAs), which contain a peptide-based backbone rather than a sugar-phosphate backbone. Other chemical modifications that the antisense oligonucleotides can contain include, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (see, e.g., Antisense Drug Technology, 2nd edition, Crooke, CRC Press 2008, which is herein incorporated by reference in its entirety). For instance, antisense oligonucleotides, particularly those of shorter lengths (e.g., less than 15 nucleotides) can comprise one or more affinity enhancing modifications, such as, but not limited to, LNAs, bicyclic nucleosides, phosphonoformates, 2' O alkyl and the like. In certain embodiments, antisense oligonucleotides useful in connection with the instant invention are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention.

In certain embodiments, the antisense oligonucleotides useful for inhibiting the activity of miRNAs miR-214, miR-199a, miR-199b, miR-409, and miR-134 are about 5 to about 50 nucleotides in length, about 10 to about 30 nucleotides in length, or about 20 to about 25 nucleotides in length. In certain embodiments, antisense oligonucleotides targeting miR-214, miR-199a, miR-199b, miR-409, and miR-134 are about 8 to about 18 nucleotides in length, and in other embodiments about 12 to 16 nucleotides in length. For example, but not by way of limitation, any 8-mer or longer that is complementary to miR-214, miR-199a, miR-199b, miR-409, or miR-134 can be used, i.e., any antimir sequence that is complementary to any consecutive sequence in miR-214, miR-199a, miR-199b, miR-409, or miR-134, starting from the 5' end of the miR to the 3' end of the mature sequence. Antisense oligonucleotides can, in certain non-limiting cases, comprise a sequence that is at least partially complementary to a mature miRNA sequence, e.g. at least about 75%, 80%, 85%, 90%, 95%, 96%, 97%, 98%, or 99% complementary to a mature miRNA sequence. In certain embodiments, the antisense oligonucleotide can be substantially complementary to a mature miRNA sequence, that is at least about 95%, 96%, 97%, 98%, or 99% complementary to a target sequence. In certain embodiments, the antisense oligonucleotide comprises a sequence that is 100% complementary to a mature miRNA sequence.

In certain embodiments, the antisense oligonucleotides useful in the instant methods can comprise a sequence that is substantially complementary to a precursor miRNA sequence (pre-miRNA) for miR-214, miR-199a, miR-199b, miR-409, or miR-134. In certain embodiments, the antisense oligonucleotide comprises a sequence that is substantially complementary to a sequence located outside the stem-loop regions of the miR-214, miR-199a, miR-199b, miR-409, or miR-134 pre-miRNA sequences.

Any of the inhibitors of miR-214, miR-199a, miR-199b, miR-409, and miR-134 described herein can be delivered to the target cell by delivering to the cell one or more expression vectors encoding one or more of the miR-214, miR-199a, miR-199b, miR-409, and miR-134 inhibitors. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention. In certain embodiments the expression vector is suitable for gene therapy of mammals, including gene therapy of humans. In certain embodiments, the nucleic acid construct according to the invention is a viral gene therapy vector. Viral gene therapy vectors are well known in the art and e.g. include vectors based on an adenovirus, and members of the Parvoviridae family, such as an adeno-associated virus (AAV), or a herpes virus, pox virus or retrovirus. In certain embodiments the viral gene therapy vector is an AAV, adenoviral or a lentiviral vector (see e.g., Gentner et al., Nature Methods 6, 63-66 (2009)).

In certain embodiments, the present invention relates to methods of inhibiting the expression and/or activity of certain microRNAs, including miR-214, miR-199a, miR-199b, miR-409, and miR-134 using RNA interference (RNAi). The phrase "RNA interference" or the term "RNAi" refer to the biological process of inhibiting or down regulating gene expression and/or activity in a cell, as is generally known in the art, and which is mediated by short interfering nucleic acid molecules, (see e.g., example Zamore and Haley, 2005, Science, 309, 15194524; Vaughn and Martienssen, 2005, Science, 309, 1525-1526; Zamore et al., 2000, Cell, 101, 25-33; Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831). Additionally, the term RNAi is meant to be equivalent to other terms used to describe sequence specific RNA interference, such as post transcriptional gene silencing, translational inhibition, transcriptional inhibition, or epigenetics. For example, siRNA molecules of the invention can be used to epigenetically silence genes at either the post-transcriptional level or the pre-transcriptional level. In a non-limiting example, epigenetic modulation of gene expression by siRNA molecules of the invention can result from siRNA mediated modification of chromatin structure or methylation patterns to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237). In another non-limiting example, modulation of gene expression and/or activity by siRNA molecules of the invention can result from siRNA mediated cleavage of RNA (either coding or non-coding RNA) via RISC, or via translational inhibition, as is known in the art or modulation can result from transcriptional inhibition (see. e.g., Janowski et al., 2005, Nature Chemical Biology, 1, 216-222).

The phrase "short interfering RNA" or "siRNA", refer to any nucleic acid molecule capable of inhibiting or down regulating gene expression and/or activity by mediating RNA interference "RNAi" or gene silencing in a sequence-specific manner. These terms can refer to both individual nucleic acid molecules, a plurality of such nucleic acid molecules, or pools of such nucleic acid molecules. In certain embodiments, the siRNA can be a double-stranded nucleic acid molecule comprising self-complementary sense and antisense strands, wherein the antisense strand comprises a nucleotide sequence that is complementary to a nucleotide sequence of miR-214, miR-199a, miR-199b, miR-409, or miR-134 or a portion thereof and the sense strand comprises a nucleotide sequence corresponding to the miR-214, miR-199a, miR-199b, miR-409, or miR-134 sequence or a portion thereof. In certain embodiments, the siRNA can be a polynucleotide with a duplex, asymmetric duplex, hairpin or asymmetric hairpin secondary structure, having self-complementary sense and antisense regions, wherein the antisense region comprises a nucleotide sequence that is complementary to a nucleotide sequence of miR-214, miR-199a, miR-199b, miR-409, or miR-134 or a portion thereof and the sense region comprises a nucleotide sequence corresponding to the sequence of miR-214, miR-199a, miR-199b, miR-409, or miR-134 or a portion thereof.

In symmetric siRNA molecules of the invention, each strand, the sense strand and antisense strand, are independently about 15 to about 40 (e.g., about 15, 16, 17, 18, 19, 20, 21, 22, 23, 24, 25, 26, 27, 28, 29, 30, 31, 32, 33, 34, 35, 36, 37, 38, 39, or 40) nucleotides in length. In asymmetric siRNA molecules, the antisense region or strand of the molecule is about 15 to about 30 (e.g., about 15, 16, 17, 18, 19, 20, 21, 22, 23, 24, 25, 26, 27, 28, 29, or 30) nucleotides in length, wherein the sense region is about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides in length.

In some embodiments, siRNA molecules of the invention have 100% complementarity between the sense strand or sense region and the antisense strand or antisense region of the siRNA molecule. In other or the same embodiments, siNA molecules of the invention are perfectly complementary to the sequence of miR-214, miR-199a, miR-199b, miR-409, or miR-134 or a portion thereof. In certain embodiments, the siRNA molecules of the invention have partial complementarity (i.e., less than 100% complementarity) between the sense strand or sense region and the antisense strand or antisense region of the siRNA molecule or between the antisense strand or antisense region of the siRNA molecule and the sequence of miR-214, miR-199a, miR-199b, miR-409, or miR-134 or a portion thereof. Thus, in some embodiments, the double-stranded nucleic acid molecules of the invention, have between about 15 to about 40 (e.g., about 15, 16, 17, 18, 19, 20, 21, 22, 23, 24, 25, 26, 27, 28, 29, 30, 31, 32, 33, 34, 35, 36, 37, 38, 39, or 40) nucleotides in one strand that are complementary to the nucleotides of the other strand. In other embodiments, the molecules have between about 15 to about 40 (e.g., about 15, 16, 17, 18, 19, 20, 21, 22, 23, 24, 25, 26, 27, 28, 29, 30, 31, 32, 33, 34, 35, 36, 37, 38, 39, or 40) nucleotides in the sense region that are complementary to the nucleotides of the antisense region of the double-stranded nucleic acid molecule. In yet other embodiments, the double-stranded nucleic acid molecules of the invention have between about 15 to about 40 (e.g., about 15, 16, 17, 18, 19, 20, 21, 22, 23, 24, 25, 26, 27, 28, 29, 30, 31, 32, 33, 34, 35, 36, 37, 38, 39, or 40) nucleotides in the antisense strand that are complementary to a nucleotide sequence of the sequence of miR-214, miR-199a, miR-199b, miR-409, or miR-134 or a portion thereof.

In certain embodiments, the siRNA molecules of the instant invention can comprise one or more modified nucleotides. The modified siRNA molecules of the invention can comprise modifications at various locations within the siRNA molecule. In some embodiments, the double-stranded siRNA molecule of the invention comprises modified nucleotides at internal base paired positions within the siRNA duplex. In certain embodiments, a double-stranded siRNA molecule of the invention comprises modified nucleotides at non-base paired or overhang regions of the siRNA molecule. In yet other embodiments, a double-stranded siRNA molecule of the invention comprises modified nucleotides at terminal positions of the siRNA molecule. For example, such terminal regions include the 3'-position and/or 5'-position of the sense and/or antisense strand or region of the siRNA molecule. Additionally, any of the modified siRNA molecules of the invention can have a modification in one or both oligonucleotide strands of the siRNA duplex, for example in the sense strand, the antisense strand, or both strands. Moreover, with regard to chemical modifications of the siRNA molecules of the invention, each strand of the double-stranded siRNA molecules of the invention can have one or more chemical modifications, such that each strand comprises a different pattern of chemical modifications.

In certain embodiments, the present invention relates to methods of inhibiting the expression and/or activity of certain microRNAs, including miR-214, miR-199a, miR-199b, miR-409, and miR-134, using catalytic nucleic acids. The term "catalytic nucleic acids" includes DNA and RNA molecules that have complementarity in a target-binding region to a specified oligonucleotide target, such as miR-214, miR-199a, miR-199b, miR-409, and/or miR-134, and an enzymatic activity which is active to specifically cleave the oligonucleotide target. Accordingly, catalytic nucleic acids molecules are capable of cleaving the oligonucleotide target, such as miR-214, miR-199a, miR-199b, miR-409, and/or miR-134, intermolecularly. This complementarity functions to allow sufficient hybridization of the catalytic nucleic acid to the target to allow the intermolecular cleavage of the target to occur.

The term "catalytic nucleic acid" as used herein encompasses enzymatic RNA or DNA molecules, enzymatic RNA-DNA polymers, and enzymatically active portions or derivatives thereof. In certain embodiments, the catalytic nucleic acid molecules of the present invention can be of varying lengths and folding patterns, as appropriate, depending on the type and function of the molecule. For example, catalytic nucleic acid molecules may be about 15 to about 400 or more nucleotides in length. In certain embodiments, the catalytic nucleic acid molecule of the present invention is between about 20 and 100 nucleotides, or 20 and 50 nucleotides, or 25 and 45 nucleotides in length. In certain embodiments, the catalytic nucleic acid molecules of the instant invention can comprise one or more modified nucleotides.

In certain embodiments, the target-binding or "recognition" domain of a catalytic nucleic acid molecule of the present invention typically comprises two nucleotide sequences flanking a catalytic domain, and typically contains a sequence of at least about 3 to about 30 bases, or about 6 to about 15 bases, which are capable of hybridizing to a complementary sequence of bases within the target nucleic acid giving the enzymatic DNA molecule its high sequence specificity. Modification or mutation of the recognition site via well-known methods allows one to alter the sequence specificity of an enzymatic nucleic acid molecule. (See Joyce et al, Nucleic Acids Res., 17:711-712, (1989), which is hereby incorporated by reference in its entirety).

Non-limiting examples of catalytic domains that can be used in the context of the catalytic nucleic acid molecules of the instant invention include catalytic domains derived from hairpin ribozymes, hammerhead ribozymes, group I intron ribozymes, ribonuclease P and hepatitis delta virus ribozymes. Specific catalytic domain sequences and techniques for incorporation of such domains into catalytic nucleic acid molecules are well known in the art. (See, e.g., Sun et al., Therapeutic Use Of Catalytic RNA And DNA, Pharmacol Rev, 52:325-347, (2000), which is hereby incorporated by reference in its entirety.)

In certain embodiments, the present invention relates to methods of increasing the expression and/or activity of certain microRNAs, including: miR-200a, miR-200b, and/or miR-192. For example, in certain embodiments, the agonist of miR-200a, miR-200b, and/or miR-192 are polynucleotides encoding a mature miR-200a, miR-200b, and/or miR-192 sequences. In certain embodiments, the agonist of miR-200a, miR-200b, and/or miR-192 can be a polynucleotide comprising the pre-miRNA sequence for miR-200a, miR-200b, and/or miR-192. Alternatively, the agonist of miR-200a, miR-200b, and/or miR-192 can be separate polynucleotides each comprising a mature sequence or pre-miRNA sequence of the miRNA. The polynucleotide comprising the mature miR-200a, miR-200b, and/or miR-192 sequence can be single stranded or double stranded. The polynucleotides can contain one or more chemical modifications, such as locked nucleic acids, peptide nucleic acids, sugar modifications, such as 2'-O-alkyl (e.g. 2'-O-methyl, 2'-O-methoxyethyl), 2'-fluoro, and 4' thiol modifications, and backbone modifications, such as one or more phosphorothioate, morpholino, or phosphor-nocarboxylate linkages. In certain embodiments, the polynucleotide comprising a miR-200a, miR-200b, and/or miR-192 sequence is conjugated to another moiety, such as, but not limited to, cholesterol.

In another embodiment, the agonist of miR-200a, miR-200b, and/or miR-192 can be encoded on an expression vector. An expression vector for expressing miR-200a, miR-200b, and/or miR-192 comprises at least one promoter operably linked to a polynucleotide encoding miR-200a, miR-200b, and/or miR-192. The polynucleotides encoding the one or more miRNA sequences can encode pre-miRNA or mature miRNA sequence(s).

In certain embodiments, a nucleic acid construct, such as an expression vector, comprising a microRNA agonist of the invention is operably linked to a mammalian cell-compatible expression control sequence, e.g., a promoter. Many such promoters are known in the art. Constitutive promoters that are broadly expressed in many cell types, such as the CMV promoter can be used. However, promoters that are inducible, tissue-specific, cell-type-specific, or cell cycle-specific can also be used.

In certain embodiments, the present invention relates to nucleic acid constructs comprising a nucleotide sequence encoding an microRNA agonist operably linked to an expression control sequence as defined herein above, wherein the construct is an expression vector that is suitable for gene therapy of mammals, including gene therapy of humans. In certain embodiments, the nucleic acid construct according to the invention is a viral gene therapy vector. Viral gene therapy vectors are well known in the art and e.g. include vectors based on an adenovirus, and members of the Parvoviridae family, such as an adeno-associated virus (AAV), or a herpes virus, pox virus or retrovirus. In certain embodiments the viral gene therapy vector is an AAV, adenoviral or a lentiviral vector. (see e.g., Gentner et al., Nature Methods 6, 63-66 (2009).

5.3.3 Pharmaceutical Compositions for Modulating EMT-Related microRNA Activity The present invention also includes pharmaceutical compositions comprising an inhibitor of miR-214, miR-199a, miR-199b, miR-409, or miR-134 or agonist of miR-200a, miR-200b, or miR-192. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

In one embodiment, the pharmaceutical composition comprises an effective dose of a miR-214, miR-199a, miR-199b, miR-409, or miR-134 inhibitor. In another embodiment, the pharmaceutical composition comprises an effective dose of a miR-200a, miR-200b, and/or miR-192 agonist. An "effective dose" is an amount sufficient to effect a beneficial or desired clinical result. An effective dose of an miRNA inhibitor or miRNA agonist of the invention can be about 1 mg/kg to about 200 mg/kg, about 20 mg/kg to about 160 mg/kg, or about 40 mg/kg to about 100 mg/kg. In one embodiment, the inhibitor of miR-214, miR-199a, miR-199b, miR-409, or miR-134 is administered each at a dosage of about 20 mg/kg to about 200 mg/kg. In another embodiment, the inhibitor of miR-214, miR-199a, miR-199b, miR-409, or miR-134 is administered each at a dosage of about 80 mg/kg. In another embodiment, the agonist of miR-200a, miR-200b, or miR-192 is administered each at a dosage of about 20 mg/kg to about 200 mg/kg. In still another embodiment, the agonist of miR-200a, miR-200b, or miR-192 is administered each at a dosage of about 80 mg/kg. The precise determination of what would be considered an effective dose can be based on factors individual to each patient, including their size, age, and nature of inhibitor or agonist (e.g., expression construct, antisense oligonucleotide, etc). Therefore, dosages can be readily ascertained by those of ordinary skill in the art from this disclosure and the knowledge in the art.

Colloidal dispersion systems, such as macromolecule complexes, nanocapsules, microspheres, beads, and lipid-based systems including oil-in-water emulsions, micelles, mixed micelles, and liposomes, can be used as delivery vehicles for the oligonucleotide inhibitors of miRNA function, polynucleotides encoding miRNA agonists, or constructs expressing particular miRNA inhibitors or agonists. Commercially available fat emulsions that are suitable for delivering the nucleic acids of the invention include Intralipid™, Liposyn™, Liposyn™ II, Liposyn™ III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. No. 5,981,505; U.S. Pat. No. 6,217,900; U.S. Pat. No. 6,383,512; U.S. Pat. No. 5,783,565; U.S. Pat. No. 7,202,227; U.S. Pat. No. 6,379,965; U.S. Pat. No. 6,127,170; U.S. Pat. No. 5,837,533; U.S. Pat. No. 6,747,014; and WO03/093449, which are herein incorporated by reference in their entireties.

One will generally desire to employ appropriate salts and buffers to render delivery vehicles stable and allow for uptake by target cells. Aqueous compositions of the present invention comprise an effective amount of the delivery vehicle comprising the inhibitor polynucleotides or miRNA polynucleotide sequences (e.g. liposomes or other complexes or expression vectors) dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or polynucleotides of the compositions.

The active compositions of the present invention can include classic pharmaceutical preparations. Administration of these compositions according to the present invention can be via any common route so long as the target tissue is available via that route. This includes oral, nasal, or buccal. Alternatively, administration can be by intradermal, subcutaneous, intramuscular, intraperitoneal or intravenous injection. Pharmaceutical compositions comprising miRNA inhibitors, polynucleotides encoding miRNA sequence or expression constructs comprising miRNA sequences can also be administered by catheter systems.

The active compounds can also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media can contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions can be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally can be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

5.3.4. Assays for Use in Connection with Anti-microRNA Therapeutic Approach

As outlined above, in Sections 5.3.1.-5.3.3., the present invention provides for methods of treating a subject, such as, but not limited to, methods comprising performing a diagnostic method as set forth herein and then, if an EMT signature is detected in a sample of the subject, and administering therapy with a microRNA expression/activity modulator.

In certain non-limiting embodiments of the present invention, one or more of the diagnostic methods set forth above, in Section 5.2., is performed and a therapeutic decision concerning the use of an anti-microRNA therapeutic approach is made in light of the results of that assay. For example, but not by way of limitation, a therapeutic decision, such as whether to prescribe a therapeutic such as those outlined in Sections 5.3.2.-5.3.3., can be made in light of the results of a diagnostic method as set forth in Section 3.2. The results of the diagnostic method are relevant to the therapeutic decision as the presence of the EMT signature or a subset of markers associated with it, in a sample from a subject can, in certain embodiments, indicate a decrease in the relative benefit conferred by a particular therapeutic intervention In certain embodiments, the high-specificity invasion and/or metastasis-sensing biomarker assay methods for use in connection with the therapeutic interventions discussed herein include, but are not limited to, the nucleic acid amplification assays; nucleic acid hybridization assays; and protein detection assays that employ the EMT biomarkers discussed in detail in Section 3.2. In certain embodiments, the assays of the present invention involve combinations of such detection techniques, e.g., but not limited to: assays that employ both amplification and hybridization to detect a change in the expression, such as overexpression or decreased expression, of a gene at the nucleic acid level; immunoassays that detect a change in the expression of a gene at the protein level; as well as combination assays comprising a nucleic acid-based detection step and a protein-based detection step.

5.4. Methods of Drug Discovery Based on the EMT Signature

In certain embodiments the instant invention can be used to develop multi-cancer invasion-inhibiting therapeutics using targets deduced from the biological knowledge provided by the EMT signature. In various non-limiting embodiments, the invention provides for methods of identifying agents that inhibit invasion and/or metastatic dissemination of a cancer in a subject. In certain of such embodiments, the methods comprise exposing a test agent to cancer cells expressing an EMT signature, wherein if the test agent decreases overexpression of genes in the signature, the test agent may be used as a therapeutic agent in inhibiting invasion and/or metastasis of a cancer.

In certain embodiments, the effect of a test agent on the expression of genes in the EMT signature that is associated with invasiveness set forth herein may be determined (e.g., but not limited to, overexpression of at least one of, at least two of, at least three of, at least four of, or at least five, at least six, or at least all seven of the genes encoding the following proteins: SNAI2, LUM, DCN, COL1A1, COL1A2, COL3A1, and COL6A3; as well as one or more or two or more or three or more of the following: COL11A1, THBS2, COL5A2, COL5A1, VCAN, FN1, SULF1, FBN1, ASPN, SPARC, CTSK, MMP2, BGN, LOXL2, TIMP3, CDH11, SERPINF1, EDNRA, ACTA2, PDGFRB, LGALS1, GLT8D2, NID2, PRRX1, and VIM, and if the test agent decreases overexpression of genes in the signature, the test agent can be used as a therapeutic agent in treating/preventing invasion and/or metastasis of a cancer.

In certain embodiments, the effect of a test agent will be assayed in connection with the expression of SNAI2. In certain embodiments, the effect of a test agent will be assayed in connection with the expression of SNAI2, LUM, and DCN. In certain embodiments, the effect of a test agent will be assayed in connection with the expression of SNAI2, LUM, DCN, COL1A1, COL1A2, COL3A1, and COL6A3.

In certain embodiments, the effect of a test agent will be assayed in connection with the expression of at least one of, at least two of, at least three of, at least four of, or at least five, at least six, or at least all seven of the following proteins: SNAI2, LUM, DCN, COL1A1, COL1A2, COL3A1, and COL6A3 and the expression of one or more microRNAs selected from the group consisting of: miR-214, miR-199a, and miR-199b.

In certain embodiments, the effect of a test agent will be assayed in connection with the expression of at least one of, at least two of, at least three of, at least four of, or at least five, at least six, or at least all seven of the following proteins: SNAI2, LUM, DCN, COL1A1, COL1A2, COL3A1, and COL6A3 and the expression of one or more microRNAs selected from the group consisting of: hsa-miR-22; hsa-miR-514-1/hsa-miR-514-2|hsa-miR-514-3; hsa-miR-152; hsa-miR-508; hsa-miR-509-1/hsa-miR-509-2/hsa-miR-509-3; hsa-miR-507; hsa-miR-509-1/hsa-miR-509-2; hsa-miR-506; hsa-miR-509-3; hsa-miR-214; hsa-miR-510; hsa-miR-199a-1/hsa-miR199a-2; hsa-miR-21; hsa-miR-513c; and hsa-miR-199b.

6. Examples

6.1. Example 1

6.1.1. Experimental Aim

Given the heterogeneity of cells in tumors, the EMT signature could reflect the superposition of several mechanisms. Among other possibilities, the cells producing the signature could be derived from multiple sources, such as the bone marrow, the local stroma, or the cancer cells after undergoing an EMT. To determine the source of the EMT, xenograft models employing human cancer cell lines implanted into NCR nude mice were used. Certain of the implanted cancer cell lines were in their original form, others were engineered to express INHBA, and others were engineered to express the activin antagonist follistatin (FST). Each of the resulting growing tumors was harvested and profiled for gene expression twice using human and mouse microarrays separately, as outlined below. The results validated that the signature was found in human, but not mouse, cells, and that its presence was independent of any transfections of the human cells with either INHBA or FST, indicating that activin signaling does not play a causal role.

6.1.2. Materials and Methods

Transfections.

NGP neuroblastoma cells containing FUW-Luciferase plasmid (kindly donated by Dr. Adolfo Ferrando) were stably co-transfected with either FST-pReceiver-Lv105 or INHBA-pReceiver-Lv105 (GeneCopoeia; Rockville, Md.).

Tumor Implantation.

The left flank was prepared in a sterile manner after anesthetizing the mice with intraperitoneal ketamine (50 mg/kg) and xylazine (5 mg/kg). An incision was made exposing the left kidney, and an inoculum of $10^6$ NGP-FUW tumor cells expressing INHBA, FST or control NGP cells suspended in 0.1 mL of phosphate-buffered saline (PBS) was injected with a 25-gauge needle. The fascia was closed with a single 4-0 polysorb suture (US Surgical Corp, Norwalk, Conn.). The experiment included 18 mice that were implanted with INHBA, FST or control NGP cells.

Harvesting of Specimens and Histology.

Mice were sacrificed when estimated tumor weight reached 1.5 g followed by collection of contralateral kidney and tumor. Tumor tissue was either snap frozen for RNA isolation or fixed in freshly prepared 4% paraformaldehyde for histology. Paraformaldehyde-fixed specimens were subsequently embedded in paraffin blocks and sectioned. Slides were stained with H&E and examined microscopically.

Microarrays and Probes.

HG-U133A 2.0 and 430 A2.0 Gene Chips (Affymetrix, Santa Clara, Calif.) were used to investigate gene expression in xenograft tumors. The cRNA probes were synthesized as recommended by Affymetrix. The cRNA was purified using RNeasy and fragmented according to the Affymetrix protocol, and 15 Ag of biotinylated cRNA were hybridized to U133A microarrays (Affymetrix). After scanning, expression values for each gene were determined using Affymetrix Gene Chip software version 4.0. Gene Spring (Silicon Genetics, Redwood City, Calif.).

Semi-Quantitative Reverse Transcription-PCR.

Total RNA was isolated from tumors by the acid/guanidinium thiocyanate method using Total RNA Isolation Kit (Ambion Inc, Austin, Tex.) followed by reverse transcription using SuperScript First-Standard synthesis System for RT-PCR from Invitrogen according to manufacture recommendations (Carlsbad, Calif. USA). Relative expression of human versus mouse COL11A1 (Hs00266273_m1, Hs01568063_m1) genes in tumor xenografts were examined by RT-PCR using indicated primers received from Applied Biosystem (Carlsbad, Calif.). Products were detected by Hot Start-IT Probe qPCR Master Mix from USB Affymetrix (Santa Clara, Calif.) according to manufacture instructions. To correct for samples variations in RT-PCR efficiency and errors in quantitation, analysis of human HPRT, CYC, ACTB, GAPD PPIA and mouse GAPD, ACTB, GUSB, HMBS, HPRT expression was used to normalize samples.

Microarray Datasets.

The data set, corresponding to 18 tumors profiled separately with human and mouse microarrays, will be available from the GEO database (http://www.ncbi.nlm.nih.gov/geo). The data were RMA normalized using the Bioconductor open source software. For FIG. 1, the TCGA ovarian cancer dataset consisting of 581 samples was downloaded from The Cancer Genome Atlas website on May 26, 2011, using the Affymetrix HG U133A level 2 data. The human body index dataset of 504 normal human samples was downloaded from Gene Expression Omnibus under accession number GSE7307 using the base-2 logarithm of the expression values.

Differential Expression Analysis.

The 18 samples were regrouped according to the expression level of human COL11A1, into 7 samples with high or intermediate COL11A1 expression values, and 11 with low COL11A1 expression values. Based on this partition, differential expression analysis was performed using significance analysis of microarrays (SAM), implemented in the Bioconductor package saw. The significantly differentially expressed genes were defined as those having simultaneously a Q-value less than 0.05 and a fold-change greater than 2.

6.1.3. Experimental Results

The presence only in human cells of overexpressed genes of the same previously-identified signature proves that the cancer cells themselves undergo an EMT. Furthermore, the continuity of the fibroblastic transition signature (FIG. 1) suggests that it reflects a dynamic and reversible process. Its potential reversal is consistent with the possibility that it is a requirement for all metastases, even though the signature is only observed in a subset of high-stage extracted samples.

Very different expression levels for most genes in human and mouse were found, suggesting that interspecies hybridization is minimal, which was confirmed with real-time PCR (see Example 1).

Figure 2:
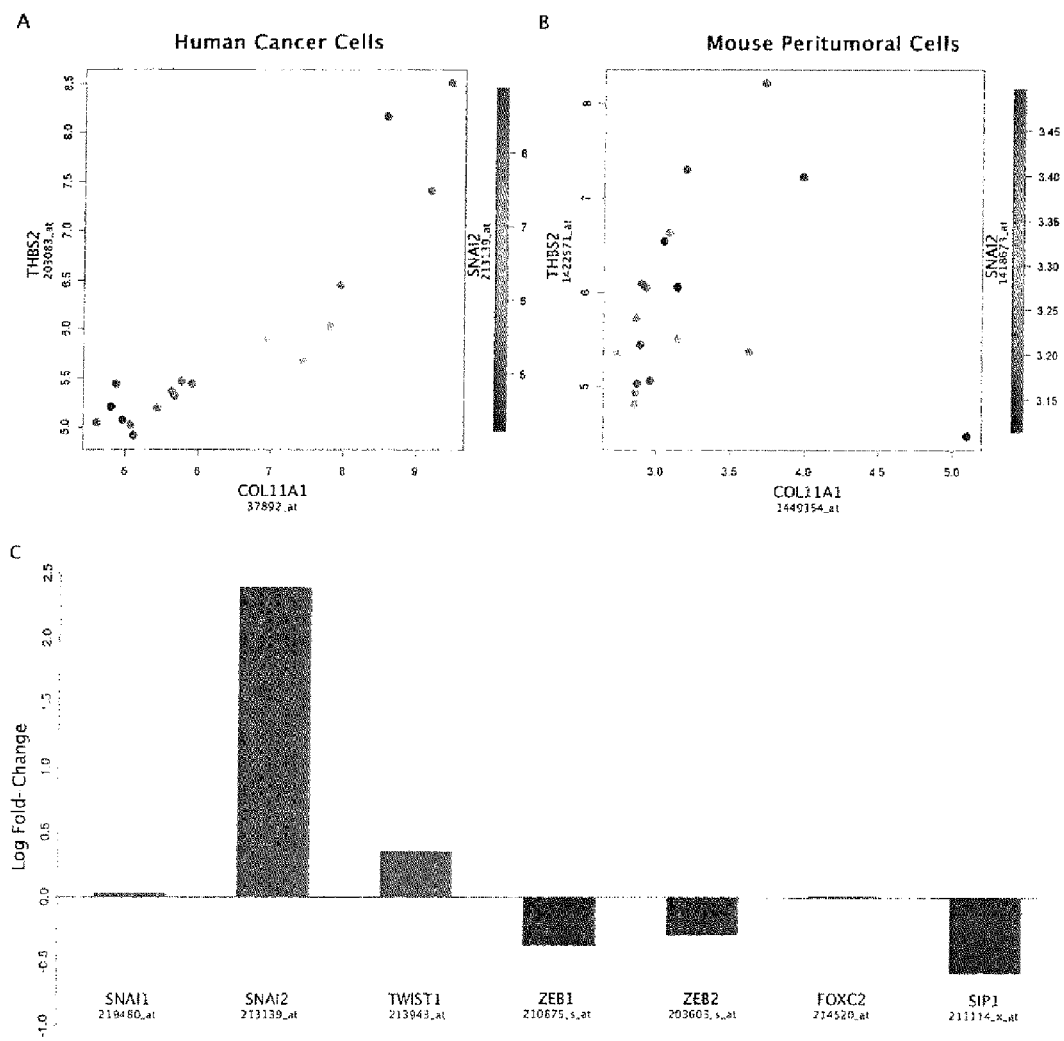

Using COL11A1 is a proxy, the 18 samples accordingly were ranked and investigated to determine if most of the EMT markers of the signature were co-expressed with COL11A1. This co-expression was identified as indeed the case in human cells only. For example, FIG. 2 shows scatter plots in human and mouse of the 18 samples for the expression of Slug (SNAI2) in terms of the expression of the main genes of the fibroblastic transition signature, COL11A1 and THBS2, demonstrating that this co-expression is clearly present in the human cells, but totally absent in the mouse cells. Specifically, seven samples had high or intermediate levels of co-expressed genes in the human cells, while the remaining 11 have relatively lower levels.

Based on this partition, 398 genes were identified as significantly (both Q<0.05 and FC>2) up-regulated, including the following 29: COL11A1, THBS2, COL5A2, COL5A1, VCAN, COL1A1, COL3A1, FN1, SULF1, FBN1, ASPN, SPARC, CTSK, MMP2, BGN, LUM, LOXL2, COL6A3, TIMP3, CDH11, SERPINF1, EDNRA, ACTA2, PDGFRB, SNAI2, LGALS1, GLT8D2, NID2, PRRX1. Also identified was VIM (vimentin). The presence in this list of SNAI2 (Slug), ACTA2 (a SMA), FN1 (fibronectin), VIM (vimentin), together with many of the other EMT markers mentioned above, indicates that some human cancer cells underwent EMT. Other EMT transcription factors (Snail, Twist, ZEB1, ZEB2) were not up-regulated.

The co-expression of the above 29 significantly up-regulated genes are shown in the heat map of FIG. 3. INHBA, the third prominent gene of the signature in addition to COL11A1 and INHBA, is not included in the list, because its expression was manipulated by the transfections with consistent results. Furthermore, as shown in the heat map, the transfection of cancer cells with either INHBA or FST did not have any effect on the presence of the signature.

6.2 Example 2

The aim of the following work is to exemplify that modulation of the expression and/or activity of certain microRNAs can inhibit EMT. In order to accomplish this aim, xenograft models employing human cancer cell lines are implanted into NCR nude mice. Certain of the implanted cancer cell lines are in their original form, while others are engineered to express specific microRNAs (thereby increasing the expression and/or activity of such microRNAs), and still others are engineered to express antisense oligonucleotides targeted to specific microRNAs (thereby decreasing the expression and/or activity of such microRNAs). Each of the resulting growing tumors is harvested and profiled for gene expression using microarrays, as outlined below.

For assays involving the increased expression and/or activity of certain microRNAs, NGP neuroblastoma cells are stably co-transfected with one or more expression vectors capable of independently or coordinately expressing one or more of miR-200a, miR-200b, and/or miR-192. For assays involving the decreased expression and/or activity of certain microRNAs, NGP neuroblastoma cells are stably co-transfected with one or more expression vectors capable of independently or coordinately expressing one or more antisense oligonucleotides capable of inhibiting the expression and/or activity of miR-214, miR-199a, miR-199b, miR-409, and/or miR-134.

The left flank of each mouse is prepared in a sterile manner after anesthetizing the mice with intraperitoneal ketamine (50 mg/kg) and xylazine (5 mg/kg). An incision is made exposing the left kidney, and an inoculum of $10^6$ NGP tumor cells expressing the particular microRNA or antisense molecule or control NGP cells suspended in 0.1 mL of phosphate-buffered saline (PBS) is injected with a 25-gauge needle. The fascia is closed with a single 4-0 polysorb suture (US Surgical Corp, Norwalk, Conn.).

Mice are sacrificed when estimated tumor weight reaches 1.5 g followed by collection of contralateral kidney and tumor. Tumor tissue is either snap frozen for RNA isolation or fixed in freshly prepared 4% paraformaldehyde for histology. Paraformaldehyde-fixed specimens are subsequently embedded in paraffin blocks and sectioned. Slides are stained with H&E and examined microscopically.

Gene Chips (Affymetrix, Santa Clara, Calif.) are used to investigate gene expression of biomarkers of EMT in xenograft tumors and cRNA probes are synthesized as recommended by Affymetrix. The cRNA is purified using RNeasy and fragmented according to the Affymetrix protocol, and 15 Ag of biotinylated cRNA are hybridized to the microarrays (Affymetrix). After scanning, expression values for each gene are determined using Affymetrix Gene Chip software version 4.0. Gene Spring (Silicon Genetics, Redwood City, Calif.).

Total RNA is isolated from tumors by the acid/guanidinium thiocyanate method using Total RNA Isolation Kit (Ambion Inc, Austin, Tex.) followed by reverse transcription using SuperScript First-Standard synthesis System for RT-PCR from Invitrogen according to manufacture recommendations (Carlsbad, Calif. USA). Relative expression of biomarkers of EMT in tumor xenografts are examined by RT-PCR. Products are detected by Hot Start-IT Probe qPCR Master Mix from USB Affymetrix (Santa Clara, Calif.) according to manufacture instructions.

6.3 Example 3

Agilent human microRNA microarrays were employed to profile the following seven xenograft samples, which had been implanted in mice, as described in the Methods section of the paper (Anastassiou et al, BMC Cancer, 11:529 (2010): [78t, 79t, 508t, 522t, 507t, 525t, 515t]. The same samples had previously been analyzed using RNA sequencing technology, and we had found the following logarithmically normalized expression values for COL11A1: [00.16 00.36 00.28 00.86 03.48 02.30 02.26], indicating that the above seven samples can be partitioned into a class comprising the former four low-expression samples, and another class comprising the remaining three high-expression samples. The corresponding logarithmically normalized expression values of the microRNAs in question are shown in Table 2, below. As observed in Table 2, microRNAs 214, 199a, 199b are consistently always co-expressed with COL11A1, and by implication by the other genes of the signature.

TABLE 2

| | Microarray Data |
|---|---|
| COL11A1: | [00.16 00.36 00.28 00.86] [03.48 02.30 02.26] |
| 214-3p: | [10.10 10.61 09.09 10.85] [12.74 12.58 12.72] |
| 214-5p: | [06.62 06.42 05.75 06.45] [07.43 08.51 08.87] |
| 199a-3p: | [13.12 13.05 12.32 13.12] [14.63 14.99 14.99] |
| 199a-5p: | [11.55 11.61 11.05 12.08] [13.69 13.98 13.98] |
| 199b-5p: | [10.40 10.38 10.14 10.29] [12.19 12.25 12.08] |
| 199b-3p: | not tested |
| 409-3p: | [09.63 09.40 09.27 09.24] [09.65 09.78 09.97] |
| 409-5p: | [07.13 06.83 07.17 07.14] [06.96 07.56 07.74] |
| 134: | [05.93 06.34 05.35 05.48] [06.17 06.03 06.37] |
| 200a-3p: | [07.52 08.03 07.50 06.97] [07.25 07.46 08.69] |
| 200a-5p: | [10.22 10.22 10.22 10.22] [10.22 10.22 01.81] |
| 200b-3p: | [08.19 08.85 08.07 07.16] [07.63 07.80 08.95] |
| 200b-5p: | [10.22 01.26 10.22 10.22] [10.22 10.22 01.87] |
| 192-3p: | [10.22 02.52 02.86 10.22] [10.22 10.22 02.47] |
| 192-5p: | [06.27 09.03 08.82 07.73] [05.54 07.20 08.65] |

Various references are cited herein which are hereby incorporated by reference in their entireties.

What is claimed is:

1. A method for detecting and treating a tumor exhibiting an epithelial-mesenchymal transition in a subject comprising determining, in a sample from the tumor of the subject, the expression level, relative to a normal subject, of a SNAI2 gene product wherein overexpression of a SNAI2 gene product is indicative of the presence of an epithelial-mesenchymal transition in the tumor, and administering an effective amount of an epithelial-mesenchymal transition inhibitor comprising: a miR-214 inhibitor.

2. The method of claim 1 further comprising determining the expression level, relative to a normal subject, of at least one gene product selected from the group consisting of: LUM, DCN, COL1A1, COL1A2, COL3A1, and COL6A3, wherein overexpression of said gene product or products is indicative of the presence of an epithelial-mesenchymal transition.

3. The method of claim 2 further comprising determining the expression level, relative to a normal subject, of one or more microRNAs selected from the group consisting of: miR-214, miR-199a, and miR-199b, wherein an altered expression level is indicative of the presence of an epithelial-mesenchymal transition.

4. The method of claim 3 wherein the expression level of said gene product or products and said miRNA or miRNAs are determined by a method comprising a processing step wherein the cells of said sample are lysed.

5. The method of claim 4, comprising the further step of purifying cell gene products and exposing said proteins to a detection agent.

6. The method of claim 4, comprising the further step of purifying cell nucleic acid and exposing said nucleic acid to a detection agent.

* * * * *

SEQUENCE LISTING

<160> NUMBER OF SEQ ID NOS: 15

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ugccugucua cacuugcugu gc                                           22

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
acagcaggca cagacaggca gu                                           22

<210> SEQ ID NO 3
<211> LENGTH: 23

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
cccaguguuc agacuaccug uuc                                            23

<210> SEQ ID NO 4
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
acaguagucu gcacauuggu ua                                             22

<210> SEQ ID NO 5
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cccaguguuu agacuaucug uuc                                            23

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
acaguagucu gcacauuggu ua                                             22

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aggttacccg agcaactttg cat                                            23

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gaatgttgct cggtgaaccc ct                                             22

<210> SEQ ID NO 9
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 9
tgtgactggt tgaccagagg gg                                              22

<210> SEQ ID NO 10
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
caucuuaccg gacagugcug ga                                              22

<210> SEQ ID NO 11
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
uaacacuguc ugguaacgau gu                                              22

<210> SEQ ID NO 12
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
caucuuacug ggcagcauug ga                                              22

<210> SEQ ID NO 13
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
uaauacugcc ugguaaugau ga                                              22

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
cugaccuaug aauugacagc c                                               21

<210> SEQ ID NO 15
<211> LENGTH: 22
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 15
cugccaauuc cauaggucac ag                                              22
```